US005486167A

United States Patent [19]
Dragoo et al.

[11] Patent Number: 5,486,167
[45] Date of Patent: Jan. 23, 1996

[54] ABSORBENT ARTICLE HAVING BLENDED MULTI-LAYER ABSORBENT STRUCTURE WITH IMPROVED INTEGRITY

[75] Inventors: Jerry L. Dragoo, Fairfield; Michael S. Bogdanski, Cincinnati; Nicholas A. Ahr, Cincinnati; John R. Noel, Cincinnati, all of Ohio

[73] Assignee: The Procter & Gamble Company, Cincinnati, Ohio

[21] Appl. No.: 427,181

[22] Filed: Apr. 12, 1995

Related U.S. Application Data

[63] ·Continuation of Ser. No. 153,739, Nov. 16, 1993, abandoned, which is a continuation-in-part of Ser. No. 911, Jan. 6, 1993, Pat. No. 5,300,054, Ser. No. 637,571, Jan. 3, 1991, abandoned, Ser. No. 810,774, Dec. 17, 1991, abandoned, Ser. No. 874,871, Apr. 28, 1992, abandoned, Ser. No. 874,872, Apr. 28, 1992, abandoned, Ser. No. 882,738, May 14, 1992, abandoned, Ser. No. 915,133, Jul. 23, 1992, Ser. No. 915,134, Jul. 23, 1992, abandoned, Ser. No. 915,201, Jul. 23, 1992, abandoned, Ser. No. 915,202, Jul. 23, 1992, abandoned, Ser. No. 915,284, Jul. 23, 1992, abandoned, Ser. No. 915,285, Jul. 23, 1992, abandoned, Ser. No. 944,764, Sep. 14, 1992, Ser. No. 957,575, Oct. 7, 1992, Ser. No. 966,240, Oct. 26, 1992, abandoned, Ser. No. 108,861, Aug. 18, 1993, Pat. No. 5,439,458, and Ser. No. 931,122, Aug. 17, 1992, Pat. No. 5,304,161, which is a continuation of Ser. No. 637,090, Jan. 3, 1991, abandoned.

[51] Int. Cl.[6] ............................ A61F 13/15; A61F 13/20
[52] U.S. Cl. .................. 604/384; 604/358; 604/366; 604/370; 604/372; 604/368; 604/378; 604/385.1
[58] Field of Search ...................... 604/358, 366, 604/368, 370, 372, 374–375, 378, 384, 385.1

[56] References Cited

U.S. PATENT DOCUMENTS

| | | |
|---|---|---|
| 2,787,271 | 4/1957 | Clark . |
| 3,545,441 | 12/1970 | Gravdahl . |
| 3,680,561 | 8/1972 | Baron ........................ 604/375 |

(List continued on next page.)

FOREIGN PATENT DOCUMENTS

| | | |
|---|---|---|
| 0176305 | 4/1986 | European Pat. Off. . |
| 0306262 | 3/1989 | European Pat. Off. . |
| 0165807 | 8/1989 | European Pat. Off. . |
| 0336578 | 10/1989 | European Pat. Off. . |
| 0359501 | 3/1990 | European Pat. Off. . |
| 0359502 | 3/1990 | European Pat. Off. . |
| 0440161A1 | 8/1991 | European Pat. Off. . |
| 0536941A3 | 4/1993 | European Pat. Off. . |
| 2-74254 | 8/1988 | Japan . |
| 2151548 | 12/1984 | United Kingdom . |
| 2215609 | 9/1989 | United Kingdom ............... 604/368 |
| WO86/05089 | 9/1986 | WIPO . |
| WO91/11164 | 8/1991 | WIPO . |
| 9111165 | 8/1991 | WIPO ........................... 604/366 |
| WO92/07985 | 5/1992 | WIPO . |

(List continued on next page.)

*Primary Examiner*—Randall L. Green
*Assistant Examiner*—P. Zuttarelli
*Attorney, Agent, or Firm*—Jeffrey V. Bamber; Kevin C. Johnson; Steven W. Miller

[57] ABSTRACT

An absorbent article, such as a diaper, sanitary napkin, adult incontinence device which has absorbent components comprised of blends of different types of fibers is provided. The absorbent components are arranged in structures that provide improved core integrity and liquid processing. The absorbent article preferably comprises a liquid pervious topsheet, a liquid impervious backsheet joined to the topsheet, an absorbent core positioned between the topsheet and the backsheet, and an acquisition layer overlying the absorbent core. The absorbent core comprises a blend of cellulosic fibers, absorbent gelling material, and fibers such as crimped synthetic fibers that form liquid stable bonds with adjacent layers. The acquisition layer also comprises at least some fibers that form liquid stable bonds with adjacent layers. The fibers that form liquid stable bonds in the absorbent core and the acquisition layer are bonded to liquid stable components. The liquid stable components can comprise the topsheet, the backsheet, and an optional intermediate liquid stable layer positioned between the acquisition layer and the absorbent core.

24 Claims, 10 Drawing Sheets

U.S. PATENT DOCUMENTS

| | | |
|---|---|---|
| 3,768,480 | 10/1973 | Mesek et al. . |
| 3,871,378 | 3/1975 | Duncan et al. . |
| 3,976,074 | 8/1976 | Fitzgerald et al. . |
| 4,047,531 | 9/1977 | Karami . |
| 4,054,141 | 10/1977 | Schwaiger et al. . |
| 4,082,886 | 4/1978 | Butterworth et al. . |
| 4,102,340 | 7/1978 | Mesek et al. ............................ 604/368 |
| 4,118,531 | 10/1978 | Hauser . |
| 4,129,132 | 12/1978 | Butterworth et al. . |
| 4,195,634 | 4/1980 | Disalvo et al. . |
| 4,219,024 | 8/1980 | Patience et al. . |
| 4,223,677 | 9/1980 | Anderson . |
| 4,397,644 | 8/1983 | Matthews et al. . |
| 4,500,315 | 2/1985 | Pieniak et al. . |
| 4,551,142 | 11/1985 | Kopolow . |
| 4,610,678 | 9/1986 | Weisman et al. . |
| 4,636,207 | 1/1987 | Buell ........................................ 604/370 |
| 4,648,876 | 3/1987 | Becker et al. . |
| 4,773,903 | 9/1988 | Weisman et al. . |
| 4,781,962 | 11/1988 | Zamarripa et al. . |
| 4,865,596 | 9/1989 | Weisman et al. . |
| 4,883,707 | 11/1989 | Newkirk ................................... 604/372 |
| 4,886,509 | 12/1989 | Mattsson . |
| 4,888,093 | 12/1989 | Dean et al. ............................. 604/375 |
| 4,950,264 | 8/1990 | Osborn, III . |
| 4,988,344 | 1/1991 | Reising et al. ......................... 604/358 |
| 5,085,914 | 2/1992 | Perdelwitz, Jr. et al. . |
| 5,088,993 | 2/1992 | Gaur . |
| 5,147,343 | 9/1992 | Kellenberger . |
| 5,147,345 | 9/1992 | Young et al. ............................ 604/374 |
| 5,149,335 | 9/1992 | Kellenberger et al. . |
| 5,217,445 | 6/1993 | Young et al. . |
| 5,231,122 | 7/1993 | Palumbo et al. . |
| 5,300,054 | 4/1994 | Feist et al. . |
| 5,350,370 | 9/1994 | Jackson et al. . |

FOREIGN PATENT DOCUMENTS

| | | |
|---|---|---|
| WO92/11830 | 7/1992 | WIPO . |
| WO92/14430 | 9/1992 | WIPO . |
| 9301779 | 2/1993 | WIPO ...................................... 604/378 |
| WO94/09737 | 5/1994 | WIPO . |

ABSORBENT ARTICLE HAVING BLENDED MULTI-LAYER ABSORBENT STRUCTURE WITH IMPROVED INTEGRITY

This application is a continuation of application Ser. No. 08/153,739 filed on Nov. 16, 1993, now abandoned; which is a continuation in part of the following patent applications: 07/931,122 filed Aug. 17, 1992, now U.S. Pat. No. 5,304,161; which is a continuation of 07/637,090 filed Jan. 3, 1991, now abandoned; and 08/000,911 filed Jan. 6, 1993, now U.S. Pat. No. 5,300,054; and 07/637,571 filed Jan. 3, 1991, now abandoned; and 07/810,774 filed Dec. 17, 1991, now abandoned; and 07/874,871 filed Apr. 28, 1992, now abandoned; and 07/874,872 filed Apr. 28, 1992, now abandoned; and 07/882,738 filed May 14, 1992, now abandoned; and 07/915,133 filed Jul. 23, 1992, now pending; and 07/915,134 filed Jul. 23, 1992, now abandoned; and 07/915,201 filed Jul. 23, 1992, now abandoned; and 07/915,202 filed Jul. 23, 1992, now abandoned; and 07/915,284 filed Jul. 23, 1992, now abandoned; and 07/915,285 filed Jul. 23, 1992, now abandoned; and 07/944,764 filed Sept. 14, 1992, now pending; 07/957,575 filed Oct. 7, 1992, now pending; 07/966,240 filed Oct. 26, 1992, now abandoned; and 08/108,861 filed Aug. 18, 1993, now U.S. Pat. No. 5,439,458.

FIELD OF THE INVENTION

The present invention relates to absorbent articles such as diapers, training pants, sanitary napkins, adult incontinence devices, and the like. More particularly, the present invention relates to absorbent articles having absorbent layers comprised of blends of different types of fibers which are arranged in structures to provide the absorbent article with improved integrity and liquid processing capabilities.

BACKGROUND OF THE INVENTION

Typically, absorbent articles comprise a liquid pervious material that faces the wearer's body, a liquid impervious material that faces the wearer's clothing, and an absorbent body or absorbent core that is sandwiched between the liquid pervious material and the liquid impervious material. In prior absorbent articles, a material comprising comminuted wood pulp, referred to as airfelt, was used in the absorbent core to absorb the liquids and other exudates deposited on the surface of the absorbent article. One of the disadvantages of using airfelt was that a thick layer of airfelt had to be used to obtain the needed capacity.

Recent attempts to improve the effectiveness of absorbent cores have included distributing particles of absorbent gelling material in the absorbent core. The absorbent capabilities of absorbent cores containing particles of absorbent gelling material are, however, often adversely affected by a phenomenon called "gel blocking". The term "gel blocking" describes a situation that occurs when a particle of absorbent gelling material is wetted and the particle swells. The swelling of a number of such particles inhibits liquid transmission into other portions of the absorbent core. Wetting of the rest of the absorbent core thereafter takes place via a very slow diffusion process. This may have the effect that the subsequent acquisition of liquid by the absorbent core becomes much slower than the discharge of the liquids to be absorbed. As a result, leakage from the absorbent article may take place well before the particles of absorbent gelling material in the absorbent core are fully saturated or before the liquid can diffuse or wick past the "blocking" particles into the rest of the absorbent core.

Another problem that exists in absorbent articles having absorbent cores comprised of airfelt, with or without absorbent gelling materials, is that such structures tend to collapse when the airfelt becomes wet. When the absorbent material collapses, it may wad up and become hard and inflexible. These problems can make the absorbent article very uncomfortable to wear and result in the loss in the ability of the absorbent article to process liquids as intended.

Wetting of the absorbent material can also cause any bonding between layers of absorbent material to lose their effectiveness and lead to the separation of such layers. In addition, any bonds between the absorbent material and the topsheet and backsheet of the absorbent article tend to lose their effectiveness when the absorbent material becomes wet. This can cause the absorbent material to become detached from the topsheet and backsheet, and to slump or slide down between the topsheet and backsheet. These problems are of particular concern in the case of diapers and brief-type incontinence garments. These garments are large in comparison to pad-type absorbent articles like sanitary napkins, and typically have absorbent material that both underlies the wearer's crotch and extends upward toward the wearer's waist. The absorbent material that extends upward toward the wearer's waist has a tendency to slump down as a result of its own liquid saturated weight when wetted.

The loss of the effectiveness of the bonds between the absorbent material and topsheet and backsheet can be observed by pulling a wet absorbent article apart. When a wetted absorbent article comprising cellulose or cellulose-based material is pulled apart, even if the cellulosic material was glued to the topsheet or backsheet, it can be observed that the majority of the cellulosic material will separate from the topsheet and backsheet leaving only a barely visible or microscopic layer of cellulosic fibers attached to the inside surfaces of the topsheet and backsheet. It is desirable to have such absorbent layers retain more of their prior to use integrity than this, and to have absorbent layers that remain more completely attached to the adjacent layers (such as the topsheet and backsheet) during use, and particularly when wetted.

In addition, the current trend is to make absorbent articles such as diapers increasingly thinner, softer, and more flexible. The thinness allows the diaper to fit the wearer's body more closely. It also allows groups of diapers to be fit into smaller, more convenient packages. For these reasons, thinner diapers are desired by many consumers.

A number of efforts have been directed toward providing improved absorbent articles and eliminating various of the above effects and/or other problems. Several patents discuss the addition of synthetic material to absorbent articles for various purposes. These include: U.S. Pat. No. 3,285,245 issued to Eldridge, et at.; U.S. Pat. No. 3,545,441 issued to Gravdahl; U.S. Pat. No. 3,976,074 issued to Fitzgerald, et al.; U.S. Pat. No. 4,047,531 issued to Karami; U.S. Pat. No. 4,054,141 issued to Schwalger, et al.; U.S. Pat. Nos. 4,082,886 and 4,129,132 issued to Butterworth, et al.; U.S. Pat. No. 4,214,582 issued to Patel; and, U.S. Pat. No. 4,219,024 issued to Patience, et al. Other efforts are described in U.S. Pat. No. 4,610,678 issued to Weisman, et al. on Sept. 9, 1986; U.S. Pat. No. 4,673,402 issued to Weisman, et at. on Jun. 16, 1987; and European Patent Application EP-A-254,476 assigned to The Procter & Gamble Company, published Jan. 27, 1988, the disclosures of which are incorporated by reference herein. One attempt to solve the comfort problem is described in U.S. Pat. No. 4,397,644 issued to Matthews, et al. Despite these efforts, the search for improved absorbent articles has continued.

A need exists for absorbent articles with improved absorbent cores, especially those which have particles of absorbent gelling material therein. In particular, a need exists for absorbent articles with absorbent material that has a reduced tendency to collapse when wetted, and for absorbent articles that optimize the use of the core material therein. In addition, a need exists for absorbent articles which have absorbent material that remains attached to the adjacent component or layer (such as the topsheet and/or the backsheet) when the absorbent article is in its intended in-use configuration and has been wetted by bodily exudates. A need also exists to make absorbent articles such as diapers increasingly thinner, softer, and more flexible.

Therefore, it is an object of the present invention to provide absorbent articles having the characteristics described above.

These and other objects of the present invention will be more readily apparent when considered in reference to the following description and when taken in conjunction with the accompanying drawings.

SUMMARY OF THE INVENTION

The present invention is directed to an absorbent article, such as a diaper, training pant, sanitary napkin, adult incontinence device, or the like which has absorbent layers comprised of blends of different types of fibers which are arranged in structures that provide improved integrity and liquid processing capabilities.

The absorbent article preferably comprises a liquid pervious topsheet, a liquid impervious backsheet joined to the topsheet, and a multi-layer absorbent structure positioned between the topsheet and the backsheet. The multi-layer absorbent structure preferably comprises three main components. These components comprise an acquisition layer, a storage layer (or "absorbent core") positioned subjacent the acquisition layer, and an optional liquid pervious, liquid stable, intermediate integrity layer positioned between the acquisition layer and the absorbent core. The acquisition layer and absorbent core comprise at least some moisture (i.e., liquid) insensitive fibers such as crimped synthetic fibers that increase the wet integrity of these two components and form liquid stable bonds to other components of the absorbent article. (The term "liquid", as used herein, includes body exudates, synthetic urine, and water. The terms "liquid stable bonds" or "wet stable bonds", refer to bonds that are not affected by the presence of liquids, that is, bonds that retain their strength and do not dissolve when wetted.) The absorbent core preferably comprises a blend of cellulosic fibers, absorbent gelling material, and crimped synthetic fibers. The crimped fibers in the absorbent core and the acquisition layer are bonded to liquid stable components (that is, components that do not lose their integrity when wetted, particularly components that have high wet tensile strengths). The liquid stable components can comprise the topsheet, the backsheet, and the intermediate liquid pervious, liquid stable layer that is positioned between the acquisition layer and the absorbent core.

The inclusion of the crimped synthetic fibers in the acquisition layer improves the integrity, acquisition rate, absorbent capacity, and the resilience of the acquisition layer. This makes the acquisition layer softer and, as explained in greater detail herein, allows the acquisition layer to be made thinner. The crimped synthetic fibers provide both improved intra-layer integrity and inter-layer integrity. This is due to the interlocking of the crimped synthetic fibers within the acquisition layer and the absorbent core and the availability of the crimped synthetic fibers on the surfaces of these layers for forming liquid stable bonds to the liquid stable components of the absorbent article. The absorbent structure, thus, provides a plurality of layers comprising interlocking matrices of liquid stable fibers that are bonded by liquid stable bonds to adjacent liquid stable components. The absorbent structure is also bonded by liquid stable bonds between the topsheet and backsheet of the absorbent article to prevent slumping of the absorbent material between the topsheet and backsheet (in other words, slumping inside the chassis of the absorbent article).

DETAILED DESCRIPTION OF THE INVENTION

1. Introduction.

The present invention relates to absorbent articles such as diapers, training pants, sanitary napkins, adult incontinence devices, and the like, which have absorbent layers comprised of blends of different types of fibers which are arranged in structures that provide improved integrity and liquid processing.

The term "diaper", as used herein, refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, including sanitary napkins and the like.

Figure 1:
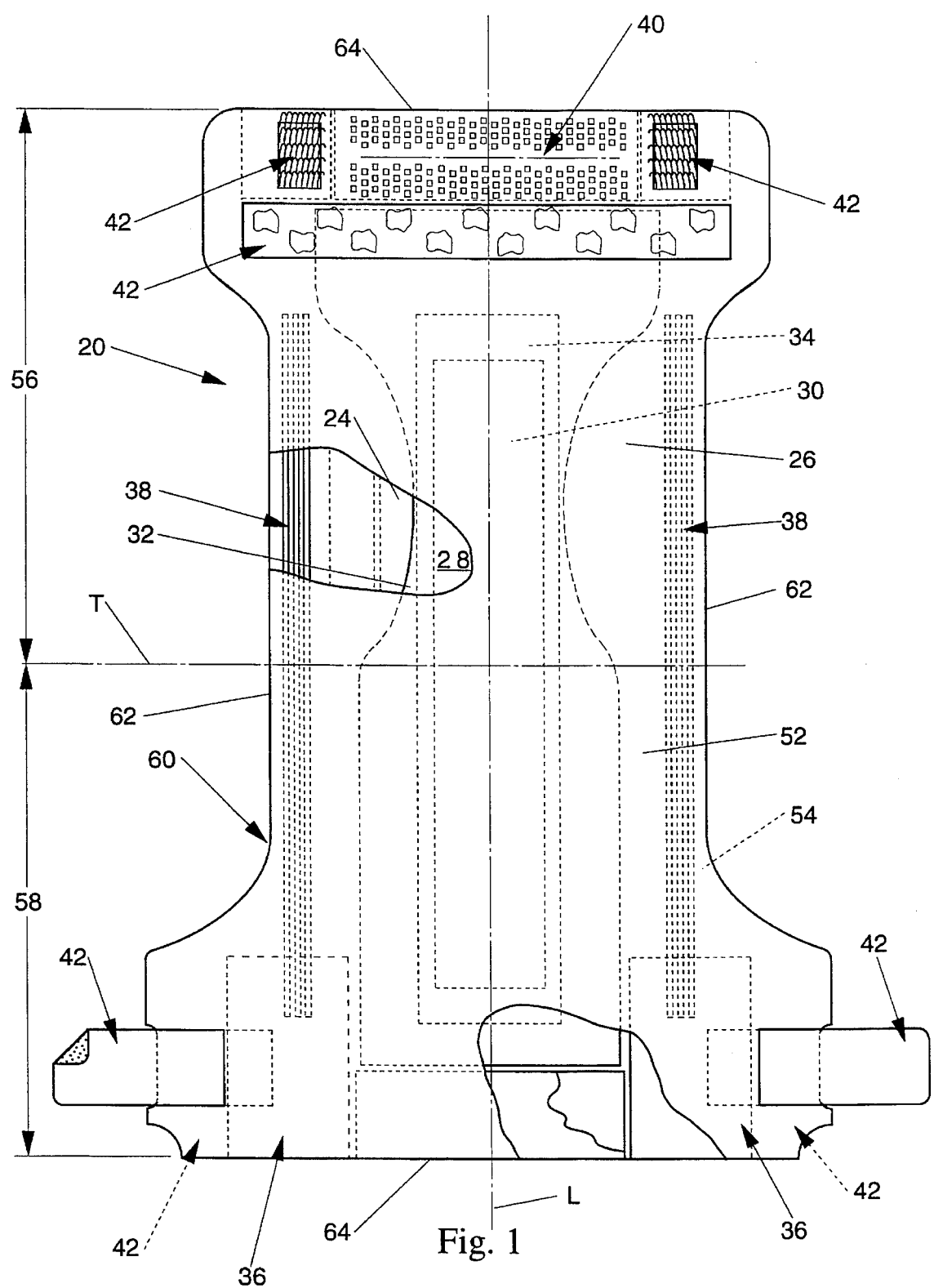
FIG. 1 is a plan view of a disposable diaper embodiment of the present invention having portions cut away to reveal the underlying structure which is shown with the backsheet of the diaper facing the viewer.

FIG. 1 is a plan view of the diaper 20 of the present invention in its flatout, uncontracted state (i.e., with elastic induced contraction pulled out) and with portions of the structure being cut-away to more clearly show the construction of the diaper 20. The outer liquid impervious surface of the diaper 20 is oriented towards the viewer. As shown in FIG. 1, the diaper 20 preferably comprises a liquid pervious topsheet 24, a liquid impervious backsheet 26 joined with the topsheet 24, and a multiple layer or "multi-layer" absorbent structure ("absorbent structure") 28 positioned between the topsheet 24 and the backsheet 26. The multilayer absorbent structure 28 preferably comprises an acquisition/distribution layer ("acquisition layer") 30, an absorbent core ("storage core") 32 preferably positioned subjacent the acquisition layer 30, and an intermediate liquid pervious, liquid stable layer 34 positioned between the acquisition layer 30 and the absorbent core 32. These three components of the multi-layer absorbent structure 28 are in liquid communication with each other. The diaper preferably also comprises elasticized side panels 36, elasticized leg cuffs 38, an elastic waist feature 40, a fastening system generally multiply designated as 42.

The diaper 20 shown in FIG. 1 has an outer surface 52, an inner surface 54 opposed to the outer surface 52, a first waist region 56, and a second waist region 58 opposed to the first waist region 56. The diaper 20 also has a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e., the inner surface 54 is generally formed by at least a portion of the topsheet 24 and other components joined to the topsheet 24). The outer surface 56 comprises that portion of the diaper 20 which is positioned away from the wearer's body (i.e., the outer surface 56 is generally formed by at least a portion of the backsheet 26 and other components joined to the backsheet 26).

The diaper 20 has two centerlines, a longitudinal centerline L and a transverse centerline T. The term "longitudinal", as used herein, refers to a line, axis, or direction in the plane of the diaper 20 that is generally aligned with (e.g., approximately parallel to) a vertical. plane which bisects a standing wearer into left and right body halves when the diaper 20 is worn. The terms "transverse" and "lateral", as used herein, are interchangeable, and refer to a line, axis, or direction which lies within the plane of the diaper 20 that is generally perpendicular to the longitudinal direction (which divides the wearer into front and back body halves).

FIG. 1 shows a preferred embodiment of the diaper 20 in which the topsheet 24 and the backsheet 26 have length and width dimensions that are generally larger than those of the multiple layer absorbent structure 28. The topsheet 24 and the backsheet 26 preferably extend beyond the edges of the multiple layer absorbent structure 28 to form the periphery 60 of the diaper 20. While the topsheet 24, the backsheet 26, and the multiple layer absorbent structure 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and in U.S. Pat. Nos. 5,151,092 and 5,221,274 both entitled "Absorbent Article With Dynamic Elastic Waist Feature Having A Predisposed Resilient Flexural Hinge", issued in the name of Kenneth B. Buell, et al. on Sept. 29, 1992 and Jun. 22, 1993, respectively.

2. Individual Components of the Absorbent Article.

The individual components of the diaper 20 will now be looked at in greater detail.

A. The Topsheet.

The topsheet 24 comprises a liquid pervious component that is placed adjacent to the wearer's body when the diaper 20 is in use. The topsheet 24 is preferably as compliant, soft feeling, and non-irritating to the wearer's skin as possible. The topsheet 24 should further exhibit good strikethrough and a reduced tendency to rewet, permitting bodily discharges to rapidly penetrate it and flow toward the multiple layer absorbent structure 28, but not allowing such discharges to flow back through the topsheet 24 to the skin of the wearer.

Figure 2:
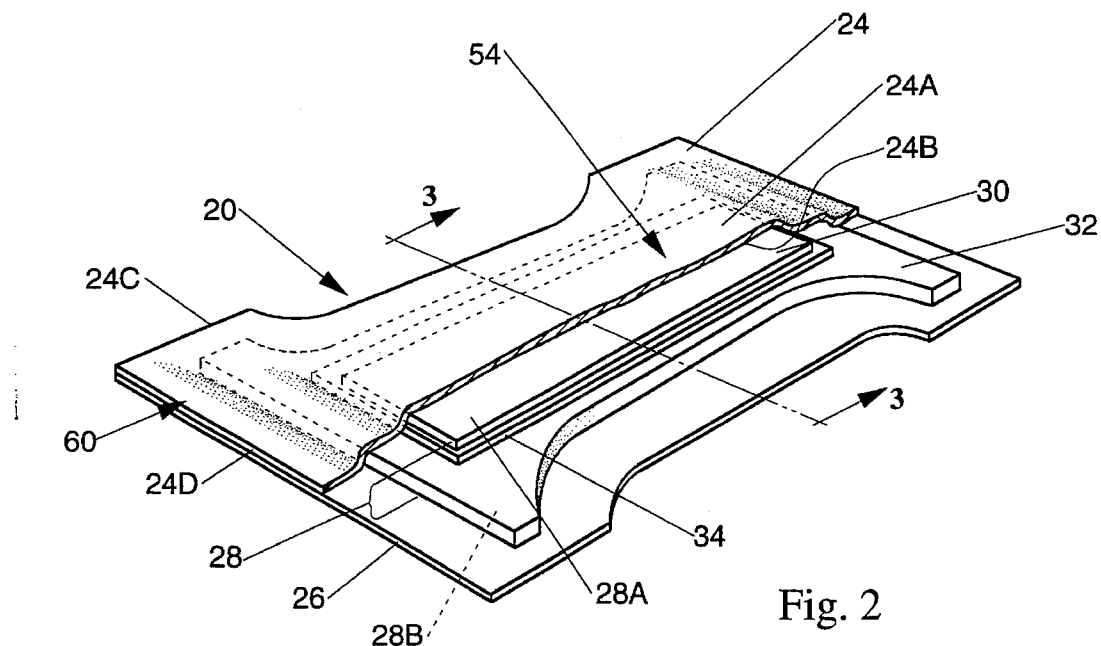
FIG. 2 is a simplified perspective view of a diaper having a preferred multiple layer absorbent structure according to the present invention with the topsheet of the diaper facing upward.

FIG. 2 shows that the topsheet 24 has two sides (or faces or surfaces), including a body-facing side 24A and an absorbent structure-facing side 24B. The body-facing side 24A of the topsheet 24 generally forms at least a portion of the inner surface 54 of the diaper 20. The topsheet 24 has two longitudinal edges 24C and two end edges 24D. (A similar numbering system may be used for the other components of the diaper. That is, the side of the component facing the wearer's body can be designated by the number of the component and a reference letter "A". The side facing away from the wearer's body can be referred to as the garment-facing side and can be designated by the number of the component and the letter "B". The side and end edges can be designated by the number of the component and the reference letters "C" and "D" respectively. )

The topsheet 24 is positioned adjacent the body surface of the multiple layer absorbent structure 28. The topsheet 24 is preferably joined to the multiple layer absorbent structure 28 and to the backsheet 26 by attachment means (shown in FIG. 3) such as those well known in the art. Suitable attachment means for this purpose are described in greater detail below in the section that discusses joining the acquisition layer to the topsheet. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60. The topsheet 24 and backsheet 26 are also indirectly joined together by directly joining them to the multiple layer absorbent structure 28 by the attachment means (shown in FIG. 3).

A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. There are a number of manufacturing techniques which may be used to manufacture the topsheet 24. For example, the topsheet 24 may be a nonwoven web of fibers that is spunbonded, carded, wet-laid, meltblown, hydroentangled, combinations of the above, or the like. A preferred topsheet is carded and thermally bonded by means well known to those skilled in the fabrics art. The topsheet 24 is preferably treated to render it hydrophilic. One preferred topsheet comprises a web of staple length polypropylene fibers such as is manufactured by Veratec, Inc., a Division of International Paper Company, of Walpole, Ma. under the designation P-8.

B. The Multiple Layer Absorbent Structure.

The multi-layer absorbent structure 28, as noted above, preferably comprises an acquisition/distribution layer ("acquisition layer") 30, an absorbent core ("storage core") 32 preferably positioned subjacent the acquisition layer 30, and an intermediate liquid stable layer (or "integrity layer") 34 positioned between the acquisition layer 30 and the storage core 32, all of which are in liquid communication with each other.

(1) The Acquisition/Distribution Layer.

The acquisition/distribution layer (which may be referred to as the "acquisition layer" or "acquisition patch") 30 is preferably positioned between the topsheet 24 and the storage core 32.

The acquisition layer 30 may be any suitable size. The acquisition layer 30 need not extend the full length or width of the storage core 32. The acquisition layer 30 can, for instance, be in the form of a strip or patch. In the embodiment shown in FIG. 2, the acquisition layer 30 is shown as a single patch (i.e., web or sheet) of nonwoven material. It should be understood, however, that the acquisition layer 30 need not be a single sheet. The terms "layer" or "web", as used herein, include, but are not limited to single unfolded sheets, folded sheets, strips of material, loose fibers, bonded fibers, multiple layers or laminates of material, or other combinations of such materials. These terms are thus, not limited to single unfolded layers or sheets of material.

In addition, in other embodiments, rather than being a separate layer that is located on top of the storage core 32, the acquisition layer 30 may be an integral layer (or component) that comprises the top layer of a laminate storage core 32 structure. In this regard, it should also be understood that the multiple layer absorbent structure 28 can be used as the entire core or it can be used as one or more layers in a layered construction. The multiple layer absorbent structure 28 can also be constructed without the acquisition layer 30.

The acquisition layer 30 serves to improve wicking (i.e., spreading) of exudates over and into the storage core 32. The acquisition layer 30 should have several characteristics. The acquisition layer 30 should be liquid permeable. The acquisition layer 30 is also preferably compliant, soft feeling, and non-irritating to the user's skin. The acquisition layer 30 has a body-facing face (or side) 30A, and an opposed garment-facing face (or side) 30B.

The overall acquisition layer 30 is preferably hydrophilic. As discussed below, the acquisition layer 30 may, however, have a hydrophobic component. The fibers (or other structural components) comprising the acquisition layer 30 may be inherently hydrophilic. Alternatively, the fibers or structural components may be treated to render them hydrophilic. Suitable methods for rendering fibers hydrophilic include treating them with a surfactant. The fibers can be treated by spraying the material comprising the acquisition layer with a surfactant or immersing the material comprising the acquisition layer into the surfactant. A more detailed discussion of such a treatment and hydrophilicity is contained in U.S. Pat. Nos. 4,988,344 and 4,988,345 issued to Reising, et at. and to Reising, respectively. The hydrophilicity of these fibers allows the acquisition layer 30 to draw liquid exudates through the topsheet 24 from below.

The acquisition layer 30 may comprise a woven material, a nonwoven material, or other suitable type of material. Preferably, the acquisition layer 30 comprises a nonwoven material. When the acquisition layer 30 comprises a nonwoven material, it can be made by a number of different processes. These include, but are not limited to the following: wet laid, airlaid, meltblown, spunbonded, carded (the latter including, thermally-bonded, through-air bonded, powder bonded, latex bonded, solvent bonded, or spun-laced). The latter processes (e.g., spunbonding and carding) may be preferred if it desired to orient the fibers in the acquisition layer because it is easier to orient the fibers in a single direction in such processes.

The materials comprising the acquisition layer 30 may be natural, synthetic, or partially natural and partially synthetic materials. Suitable natural fibers include cotton, cellulose, or other natural fibers. Suitable synthetic fibers include polyester, polypropylene, polyethylene, nylon, viscous rayon fibers, or cellulose acetate, with polyester fibers being preferred, and polyethylene terephthalate (or PET) being especially preferred. The acquisition layer 30 may also be at least partially comprised of chemically modified natural fibers such as cross-linked cellulose fibers. Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,898,642, issued Feb. 6, 1990 to Moore, et at.; U.S. Pat. No. 4,935,022 issued Jun. 19, 1990 to Lash, et al.; U.S. Pat. No. 5,137,537 issued to Herron, et al. on Aug. 11, 1992; and U.S. Pat. No. 5,183,707 issued to Herron, et al. (It should be understood, however, that cross-linked cellulose fibers are sufficiently modified that they may no longer be considered to be either cellulosic, or as natural fibers, per se.)

The acquisition layer 30 may also be comprised of capillary channel fibers (that is, fibers having channels formed therein, or thereon, and preferably on their exterior surfaces). Such fibers are described in greater detail in EPO Patent Application 0 391,814 published Oct. 10, 1990, and in U.S. Pat. No. 5,200,248 issued to Thompson, et al. on Apr. 6, 1993. The acquisition layer 30 can also be comprised of combinations of any of the foregoing materials, blends of fibers similar to those described below for use in the absorbent core, or any equivalent material or combinations of materials.

In one preferred embodiment for use in the diaper 20, the acquisition layer 30 comprises at least some fibers that form liquid stable bonds. The term "liquid stable bonds", as used herein, refers to bonds that are not affected by the presence of liquids. Preferred fibers for forming liquid stable bonds are synthetic fibers, with crimped synthetic fibers being especially preferred for providing the acquisition layer 30 with softness and resiliency. Crimped synthetic fibers are also preferred because they can interlock to provide the acquisition layer 30 with increased integrity. The acquisition layer 30 shown in FIG. 3 preferably comprises a blend of crimped synthetic fibers 48 and either natural fibers or cross-linked cellulosic fibers. The latter two types of fibers are generically designated by reference number 44.

In one preferred embodiment, the acquisition layer 30 comprises a blended layer comprising a homogeneous airlaid mixture of about 20% by weight crimped hydrophobic PET fibers and about 80% by weight of either airfelt or cross-linked cellulosic fibers. The PET fibers preferably have a denier per fiber of about 15, an uncrimped length of about 0.5 inch (about 1.3 cm), a crimp frequency of about 6 crimps per lineal inch (2.54 cm), and a crimp angle of about 88°. (All percentages specified in this description are by weight unless stated otherwise.)

While the preferred material for the crimped fibers in this embodiment is PET, in alternative embodiments the composition of the crimped fibers can be any non-water absorbing material which has a wet stiffness similar to PET. Other suitable materials for use as the crimped fibers include, but are not limited to polypropylene, nylon, polyethylene, and hi-component fibers. In addition, the denier of the fibers preferably ranges from about 1 ½ or 2 dpf to about 30 dpf. The uncrimped length of the fibers preferably ranges from about 0.25 inch (about 0.6 cm) to about 2 inches (about 5 cm). The crimp frequency is preferably between about 5 and about 15 crimps per lineal inch. The crimp angle preferably ranges from about 60° to about 100°. The amount of crimped fibers in the acquisition layer can range from about 5% to about 90%, and to be practical for use in disposable absorbent articles from a cost standpoint preferably ranges from about 10% to about 50%, and most preferably about 20% to about 40% by weight.

The acquisition layer 30 may be substantially undensified during the process of manufacturing the diaper. In alternative embodiments, the acquisition layer 30 may be densified by compressing it to densities ranging up to as high as about 4.8 g/cubic inch (about 0.3 g/cm³), or more. The acquisition layer 30 may, in either case, then be compressed during the process of placing groups of diapers into a bag for retail sale. It should be noted, that if the diaper 20 is placed into the bag in a compressed condition, it will typically expand upon removal from the bag due to the resiliency of the crimped fibers.

In alternative embodiments, it is also possible that crimped hydrophilic fibers would provide many of the benefits described herein. In addition, in other alternative embodiments, capillary channel fibers, especially curled capillary channel fibers, can be used in place of or in addition to crimped synthetic fibers. In different embodiments, the fibers in the acquisition layer (and other layers of the multiple layer absorbent structure) can also be held together in alternative manners. For example, the fibers in each layer can either be mechanically entangled, or if bicomponent fibers are used, the fibers within the layers can be bonded together by thermal bonds.

Further variations may be desirable when the acquisition layer 30 is used in other types of absorbent articles. In one embodiment which is preferred when the absorbent article comprises a sanitary napkin, the acquisition layer 30 preferably comprises a spunlace nonwoven web comprised of permanently wettable fibers. Preferably, the acquisition layer 30 is a 30 g/yard2 (35 g/m²) PET spunlace nonwoven web. Spunlaced fabrics of this type are manufactured by the Veratec Company of Walpole, Ma. The spunlace nonwoven web is formed in such a way that most of the fibers are oriented in a single direction, such as the longitudinal direction, for preferential wielding. The fibers of this preferred acquisition layer 30 material are made of a PET resin and are coated with a proprietary permanently wettable finish known as CELWET. These fibers are obtained from the Hoechst Celanese Corporation of Charlotte, N.C.

The acquisition layer 30 is preferably secured in contact with the topsheet 24 by applying adhesive between the acquisition layer 30 and the topsheet 24. The adhesive is shown schematically as layer 66 in FIG. 3. Securing the acquisition layer 30 to the topsheet 34 results in liquid penetrating topsheet 24 faster. It also prevents the absorbent material in the acquisition layer 30 from slumping between the topsheet 24 and backsheet 26.

The means for securing the acquisition layer to the topsheet is not limited to adhesives, however. The topsheet 24 and acquisition layer 30 (or other underlying layer) may also be secured at least partially by any other suitable attachment means or combinations of such other means and adhesive attachment means. For instance, in other embodiments, the topsheet 24 and acquisition layer 30 may be at least partially attached by mechanical and thermo-mechanical entanglement. Other suitable means for securing the topsheet 24 to an underlying layer are described in PCT Patent Publication No. WO 93/11725 published in the name of Cree, et al. on Jun. 24, 1993 and its corresponding U.S. patent application.

When adhesives are used to maintain the topsheet 24 in contact with the acquisition layer (or other underlying layer), the adhesive should not interfere with the transfer of liquids from the topsheet to the underlying acquisition layer or other underlying layers. The adhesives can be applied in a uniform continuous layer like meltblown fibers of adhesive, or a patterned layer, an array of separate lines, spirals, or spots of adhesive. The adhesive attachment means preferably comprises an open pattern network of filaments of adhesive as is disclosed in U.S. Pat. No. 4,573,986 issued to Minetola, et al. on Mar. 4, 1986, or an open pattern network of filaments comprising several lines of adhesive filaments swirled into a spiral pattern as illustrated by the apparatus and method shown in: U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Suitable adhesives are manufactured by the Findley Adhesives Incorporated of Elm Grove, Wi. and marketed as H-1077 or H-1137.

(2) The Intermediate Liquid Stable Layer

The optional intermediate liquid stable layer 34 is preferably located between the acquisition layer 30 and the storage core 32. The liquid stable layer 34 serves two main purposes. The liquid stable layer 34 serves as a supporting substrate for the adjacent acquisition layer 30 and the storage core 32. The liquid stable layer 34 provides a structure to which liquid stable bonds can be formed with the synthetic fibers in the acquisition layer 30 and storage core 32. The liquid stable layer 34, like the acquisition layer, need not extend the full length or width of the storage core 32.

The liquid stable layer 34 preferably has several characteristics. The liquid stable layer 34 preferably retains a high degree of its integrity when wet. The liquid stable layer 34 should not interfere with liquid movement from the acquisition layer 30 into the storage core 32. Thus, a very porous and hydrophilic material is preferred for the liquid stable layer 34. The liquid stable layer 34 is also preferably flexible so that the flexibility of the diaper is substantially unaffected by the presence of the liquid stable layer 34. In one preferred embodiment, the liquid stable layer 34 is a spunbonded polyester nonwoven web.

A commercially available spunbonded polyester nonwoven web suitable for use as the liquid stable layer is a material known as REEMAY 2055 sold by Reemay, Incorporated of Old Hickory, Tn. This material has a basis weight of about 0.55 oz./yd² (about 18.6 g/m²) and is comprised of 4 denier per fiber trilobal cross-sectionally shaped fibers. The REEMAY web is similar to the material that is used in BOUNCE dryer sheets manufactured by The Procter & Gamble Company of Cincinnati, Oh. under U.S. Pat. Nos. 4,073,996, 4,237,155, and 5,094,761. A key factor in selecting the polyester nonwoven web is its perviousness. The REEMAY web also contains inter-fiber spaces that are of sufficient size to permit some of the fibers in the acquisition layer 30 to penetrate into the storage core 32 and some of the fibers in the storage core 32 to penetrate into the acquisition layer 30.

In alternative embodiments, the liquid stable layer 34 can be comprised of other non-water absorbing materials that are similar to polyester. Examples of suitable materials for use as the liquid stable layer 34 include, but are not limited to polypropylene, nylon, and polyethylene. In addition, in other embodiments instead of using synthetic materials as the liquid stable layer, the liquid stable layer can comprise a high wet strength, low stretch (i.e., low extensibility), tissue provided in a structure in which the bonds between the high wet strength tissue and the adjacent acquisition layer 30 and storage core 32 remain strong when wet.

Such a tissue preferably has a wet tensile strength of between at least about two to four times that of tissue layers currently used in Procter & Gamble's diapers. (Such current tissues may, for instance, have a wet tensile strength of about 50 g/in. in the lateral direction and about 125 g/in. in the longitudinal direction.) Thus, the high wet tensile strength tissue should preferably have a wet tensile strength of at least between about 100 g/in. and about 200 g/in. in the lateral direction, and at least between about 250 g/in. and about 500 g/in. in the longitudinal direction. Methods for making high wet strength tissues are known in the art. These methods include, but are not limited to adding a wet strength binder such as Kymine during the wet stage of the paper making process in which the tissue is made.

The bonds between the high wet strength tissue and the adjacent acquisition layer 30 and storage core 32 must, as noted above, remain strong when wet. This represents a problem since high wet strength tissues are still comprised of cellulosic fibers which form bonds to adjacent layers that lose their strength when wet. This problem, however, can be solved by utilizing adhesives that remain in a liquid state for a longer period of time after application and tend to soak into cellulose fibers. Such adhesives tend to have a higher wet strength than ordinary pressure sensitive adhesives and do not dissolve when wet. Suitable high wet strength adhesives include Findley Adhesive H4071-01 available from the Findley Adhesive Company of Elm Grove, Wi. and Fuller adhesive HL1376X available from the H. B. Fuller Co. of St. Paul, Mn.

In addition, in other alternative embodiments, the liquid stable layer 34 can be a nonwoven material made by another suitable process. Other suitable processes for making nonwoven materials, such as carding processes, are described herein. In still other embodiments, the liquid stable layer 34 can be some type of material other than a nonwoven web. For instance, instead of comprising a nonwoven web, the liquid stable layer 34 can comprise a scrim or a net.

Further, the location of the liquid stable layer 34 within the absorbent article can vary in different embodiments. The liquid stable layer 34 is preferably positioned between the acquisition layer 30 and the storage core 32. In other embodiments, however, the liquid stable layer 34 can be positioned adjacent other faces of the components of the multi-layer absorbent structure 28. Further, if the components of the multi-layer absorbent structure 28 such as the acquisition layer and storage core comprise more than one layer, the liquid stable layer 34 can be positioned between the layers comprising such components. In still other alternative embodiments, the liquid stable layer 34 can comprise more than one layer. In this case, the additional layers could be inserted between any of the components of the diaper.

In still other alternative embodiments, the liquid stable layer 34 can be eliminated, in which case the synthetic fibers in the acquisition layer 30 and storage core 32 can be bonded directly to each other. In these latter embodiments, the moisture insensitive fibers in the acquisition layer 30 will be bonded to other moisture insensitive fibers, the synthetic fibers in the storage core 32.

(3) The Storage Core.

The storage core 32 is preferably positioned between the acquisition layer 30 and the backsheet 26. The storage core 28 provides the means for absorbing and containing urine and other body exudates. The storage core 32 is absorbent and generally at least slightly resiliently compressible (but preferably not collapsible), conformable, and non-irritating to the user's skin.

The storage core 32 used in the diaper 20 of the present invention may be referred to as a "blended" core. The storage core 32 comprises a web or batt of fibers, preferably in the form of a homogeneous blend of fibers. The blended storage core 32 is comprised of at least two groups (or types) of fibers. These include a first group (or type) of fibers and a second group (or type) of fibers. The first group of fibers comprises low denier, relatively short, hydrophilic fibers. The second group of fibers comprises from about 5% by weight of the fibers in the storage core, preferably at least about 10 or 20% to about 90%, by weight of the fibers in the storage core, of higher denier, longer, moisture insensitive synthetic fibers. (The percentage of fibers in the storage core refers to the relative weight of the fibers only, and does not include the weight of any absorbent gelling material.) The blend ratio of the two groups of fibers can be varied to produce the particular properties desired for different types of absorbent articles. These components and properties of the storage core 32 are discussed in greater detail below.

(a) The First Group of Fibers

The fibers in the first group of fibers may have various lengths and deniers provided that these properties of the fibers are less than those of the fibers in the second group of fibers. The fibers in the first group of fibers preferably have a length of less than or equal to about ½ inch (about 1.3 cm), more preferably less than or equal to about ¼ inch (about 0.6 cm). The fibers in the first group of fibers preferably have a denier per fiber (or per filament) of less than or equal to about 15, more preferably less than or equal to about 10, and most preferably less than or equal to about 2.

The first group of fibers can comprise natural fibers such as cotton or cellulose. The cellulose fibers may be in the form of comminuted wood pulp fibers known as airfelt. The first group of fibers can alternatively or additionally comprise synthetic fibers, including but not limited to, PET, polypropylene, polyethylene, rayon, chemical thermal mechanical pulp (or "CTMP" or "TMP"). ground wood, or cross-linked cellulose fibers. The fibers in the first group of fibers are either inherently hydrophilic, or they may be rendered hydrophilic by treating them in any of the manners described previously.

Performance is improved by selecting a relatively stiff fiber which maintains a substantial portion of its compression resistance when wetted for the fibers in the first group. (That is, the fibers should have a high compressive modulus.) Preferably, the fibers selected are both compression resistant under wet and dry conditions, and are wet and dry resilient (i.e., they tend to both resist compression and to spring back when compressed). Cross-linked cellulose fibers are especially preferred for these criteria.

(b) The Second Group of Fibers

The fibers in the second group of fibers are generally longer than the fibers in the first group of fibers. The fibers in the second group of fibers should also be of high compressive modulus and should maintain a relatively high modulus when wetted. The fibers in the second group of fibers should also preferably be wet and dry resilient. Suitable fibers for inclusion in the second group of fibers include, but are not limited to synthetic fibers comprised of any of those materials specified above as being suitable for use as the fibers of the acquisition layer 30. (Fiber lengths, denier, etc. may be the same, but are not necessarily the same. For example, the synthetic fibers in the acquisition layer may have one denier (e.g., a denier of about 15) for aiding in the acquisition of liquids and for greater resiliency, and the synthetic fibers in the storage core may have a lower denier, such as about 2. Some preferred fiber lengths, etc. for the synthetic fibers in the storage core are described below.)

Preferably, the fibers in the second group of fibers have an uncrimped length of greater than or equal to about ¼ inch (about 0.6 cm) long, more preferably greater than or equal to about ½ inch (about 1.3 cm). The denier of the fibers in the second group of fibers is preferably greater than the denier of the fibers in the first group of fibers. The fibers in the second group of fibers preferably have a denier per fiber of between about 1 ½ or 2 and about 50 or 60, and more preferably between about 6 and about 40. More preferably still, the denier of the fibers in the second group of fibers is between about 12 or 15 and about 30, and most preferably is between about 12 and about 25.

The fibers in the second group of fibers are liquid insensitive. That is, the fibers in the second group of fibers are not substantially affected by the presence of moisture (and, thus, will not collapse when wetted). These fibers may, however, transport liquids along their surfaces. The fibers in the second group may be hydrophilic, hydrophobic, or partially hydrophilic and partially hydrophobic. The fibers in the second group of fibers preferably have at least some hydrophilic component (which may be a cellulosic component). The fibers in the second group of fibers can be provided with a hydrophilic component in a number of suitable ways. These include, but are not limited to coating or treating the fibers to render them, or at least their surfaces, hydrophilic.

One suitable type of synthetic fibers for use in the second group of fibers is crimped polyester fibers. Suitable synthetic fibers are those formerly available from Eastman Kodak Textile Fibers Division Kingsport, Tn. as the KODEL 200 and 400 Series PET fibers. One suitable type of synthetic binder fiber is the KODEL 410 fiber. A suitable polyester fiber is the KODEL 431 fiber. These KODEL fibers have a denier of 15 per filament and a length of about 0.5 inch (about 1.3 cm) and are preferably crimped at a crimping frequency of between about 5 and 8, preferably about 6, more preferably 6.3 crimps per linear inch (i.e., per 2.5 cm). The fibers are preferably crimped at a crimping angle of between about 70° to about 91°, more preferably about 88°. Crimping provides the fibers with improved resilience, among other desired properties. The fibers may be coated with a hydrophilic or hydrophobic finish by any suitable method known in the art.

In alternative embodiments, it is possible to replace the natural fibers in the first group of fibers with very short, low denier, synthetic fibers (with hydrophilic surfaces). The blended storage core 32 in such embodiments would consist of short, low denier, hydrophilic first group of synthetic fibers (such as polyester fibers with a CELWET finish) and long, high denier second group of crimped synthetic fibers.

The storage core 32 can additionally comprise any other types of materials used in the art in absorbent articles. Examples of suitable additional core materials include creped cellulose wadding, peat moss, etc., or any equivalent material or combinations of materials.

(c) Absorbent Gelling Material

The blended storage core 32 may, and preferably does, also contain hydrogel-forming polymer gelling agents (or "absorbent gelling materials") to increase the absorptive capacity of the core.

Figure 3:
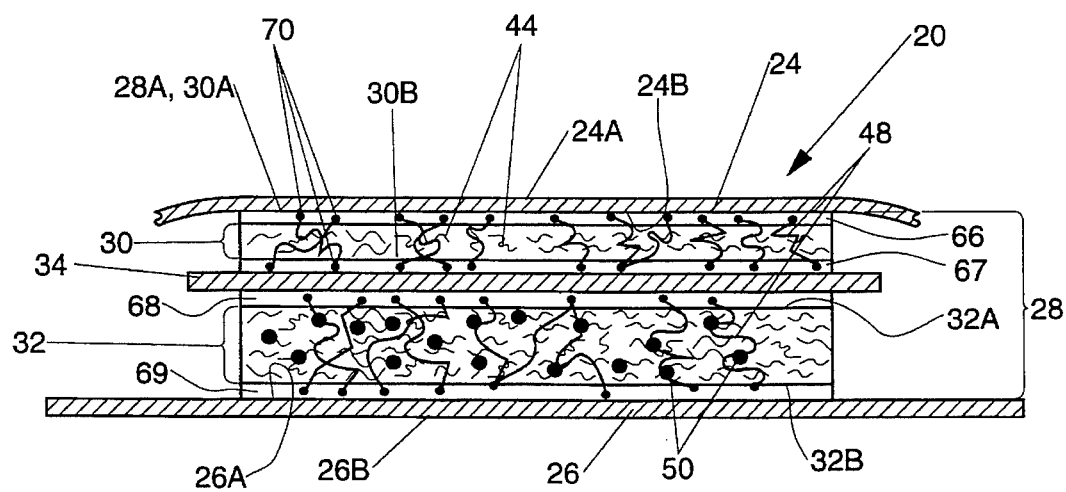
FIG. 3 is a simplified schematic and enlarged cross-sectional view of the diaper shown in FIG. 2 taken along line 3—3 of FIG. 2.

The absorbent gelling material which is employed in the storage core 32 can be in any form, such as in the form of particles, flakes, or fibers. The absorbent gelling material is shown in FIG. 3 in the form of particles 50. The characteristics of preferred types of absorbent gelling materials used therein, and types of methods which can be used for preparing these polymer particles) are described in greater detail in U.S. Pat. No. 32,649 reissued to Brandt, et al. on Apr. 19, 1988. Other preferred types of absorbent gelling materials are described in Application Ser. Nos. 07/684,712, 07/684,633, and 07/685,255 filed in the name of Roe on Apr. 12, 1991 (consolidated in PCT International Publication No. WO 92/18171 entitled "Absorbent Structure Containing Specific Particle Size Distributions of Superabsorbent Hydrogel-Forming Materials" published in the name of Roe, et al. on Oct. 29, 1992).

The storage core 32 preferably comprises between about 30% to about 95% absorbent gelling material and between about 5% to about 70% of a carrier material (preferably the blended fibrous carrier materials described above). In one particularly preferred embodiment, the storage core comprises a homogeneous air laid blend of about 11.2 grams of airfelt (about 47% of the weight of the storage core), about 2.8 grams of PET fibers (about 12% of the weight of the storage core), and about 9.6 grams of absorbent gelling material particles (about 40 or 41% of the weight of the storage core). The utilization of absorbent gelling materials is believed to be improved in the blended core. The use of higher concentrations of absorbent gelling materials is also believed to be possible (e.g., greater than or equal to about 50%, 60%, 70%, 80%, or 90%).

One particularly preferred absorbent gelling material for use in the storage core is an absorbent gelling material known as L-76LF (low fines) Lot #2T12, manufactured by Nippon Shokubai Co., Ltd of Osaka, Japan. This preferred absorbent gelling material is a non-agglomerated, surface cross-linked absorbent gelling material having a gel volume for absorbing synthetic urine of about 41.6 grams per dry gram, and about 10% extractables. This absorbent gelling material has the following particle size distribution determined under the method specified in the aforementioned U.S. Patent Applications filed in the name of Roe, et al. on Apr. 12, 1991:

| Sieve No. (U.S. Standard) | Weight % |
| --- | --- |
| on 20 | 0 |
| on 30 | 4.1 |
| on 50 | 63.5 |
| on 100 | 23.6 |
| on 325 | 8.5 |
| through 325 | .3 |

The aforementioned properties of the absorbent gelling material are determined in accordance with the methods set out in U.S. Pat. No. 32,649, Brandt, with certain modifications.

Gel volume is determined by the method described in the Brandt patent using a Jayco synthetic urine known as SynUrine instead of the synthetic urine described in the Brantit patent. Jayco synthetic urine is prepared by dissolving a mixture of 2.0 g KCl, 2.0 g $Na_2SO_4$, 0.85 g $NH_4H_2PO_4$, 0.15 g $(NH_4)_2HPO_4$, 0.19 g $CaCl_2$ and 0.23 g $MgCl_2$ to 1.0 liters of distilled water. All of the chemicals are of reagent grade. The pH of the synthetic urine is in the range of 6.0 to 6.4. The SynUrine mixture can now be obtained from Endovations, Reading, Pa. (catalog number JA-00131-000-01). The gel volume is calculated on a dry-weight basis. The dry weight used in the gel volume calculation is determined by oven drying the absorbent gelling material at 105° C. for three hours.

The percentage of extractables is determined by the Carboxylic Acid Based Hydrogel-Forming Polymers method described in the Brantit patent using 0.9% saline in place of the synthetic urine described in the Brandt patent, filtering the supernatent through a Whatman 0.7 micron GF/F glass microfiber filter (e.g. Catalog #1825-125) or equivalent, and calculating the extractable polymer on a dry-weight basis. It is also noted that in the Brantit patent $V_a$ should refer to the volume of base and $V_b$ should refer to the volume of acid.

In other preferred embodiments, the hydrogel-forming polymer gelling agents may comprise "high-speed" absorbent gelling materials. The term "high-speed" absorbent gelling materials, as used herein, means those absorbent gelling materials that are capable of absorbing exudates at such a rate that they reach at least about 40%, preferably at least about 50%, and most preferably at least about 90% of their capacity in less than or equal to about 10 seconds. A suitable method for the percent rate of capacity is described in allowed application Ser. No. 07/637,090 filed by Noel, et al. on Jan. 3, 1991 (PCT International Publication No. WO 92/11830) published on Jul. 23, 1992. In alternative embodiments, it is also possible for the high-speed absorbent gelling materials to be mixed with other types (or ordinary speed) absorbent gelling materials.

Preferably, in the embodiment described immediately above, the high-speed absorbent gelling materials are in fibrous form. Fibrous absorbent gelling material (though not necessarily high-speed fibrous absorbent gelling materials) are discussed more fully in U.S. Pat. No. 4,855,179, issued Aug. 8, 1989, to Bourland, et al. The term "fibrous absorbent gelling materials", as used herein, is intended to include absorbent gelling materials in the form of fibers that are comprised entirely of absorbent gelling material, and bi-component fibers that are comprised at least partially of other materials which have their surfaces coated with absorbent gelling materials. Suitable fibrous absorbent gelling materials include an acrylic fibrous material available under the tradename LANSEAL F from the Choli Company, LTD., of Higashi, Osaka, Japan, and a carboxymethylcellulose fibrous material available under the tradename AQUALON C from Hercules, Inc. Suitable high speed fibrous absorbent gelling materials are those known as FIBERSORB SA7000 or SA7200 formerly manufactured by Arco Chemical Company of Newton Square, Pa. and those known as OASIS manufactured by Courtaulds Fibers/Allied Colloids, a joint venture company, West Midlands, England.

In still other embodiments, the absorbent gelling material can be in the form of aggregates, or macrostructures such as sheets or strips. These macrostructures are typically prepared by forming the particulate absorbent gelling material into an aggregate, treating the aggregated material with a suitable crossslinking agent, compacting the treated aggregate to densify it and form a coherent mass, and then curing the compacted aggregate to cause the crosslinking agent to react with the particulate absorbent gelling material to form a composite, porous absorbent macrostructure. Examples of such absorbent aggregates and macrostructures and methods of making the same are disclosed in U.S. Pat. No. 5,102,597 issued to Roe, et al. on Apr. 7, 1992, U.S. Pat. No. 5,124,188 issued to Roe, et at. on Jun. 23, 1992, U.S. Pat. No. 5,149,334 issued to Lahrman, et al. on Sept. 22, 1992, and U.S. Pat. No. 5,180,662 issued to Berg, et al. on Jan. 19, 1993.

If the absorbent gelling material comprises an aggregate, crimped synthetic fibers can be mixed with the aggregate to form a layer. If the macrostructure comprises a sheet or strip, the sheet or strip will typically simply be used as another layer in the multiple layer absorbent structure. For example, such a layer may be placed between the acquisition layer 30 and the storage core 32 (or between any of the other layers of the multiple layer absorbent structure). The sheet or strip of absorbent gelling material may optionally have a liquid stable layer 34 on one side or preferably on both sides.

(d) Densification of the Storage Core

The blended storage core 32 is preferably compressed to a density of at least about 1.5 g/cubic inch (about 0.09 $g/cm^3$). The blended core 32 may be compressed to densities at least as high as about 4.0 g/cubic inch (about 0.25 $g/cm^3$) to improve fluid wicking (that is, distribution of liquids to other parts of the storage core) while still maintaining good softness and flexibility. The blended storage core 32 may be compressed to densities up to as high as about 5.6 $g/in^3$ to about 6.4 $g/in^3$ (about 0.35 $g/cm^3$ to about 0.40 $g/cm^3$). These higher density cores may become rather stiff, however. Therefore, if the storage core is compressed to densities of about 0.35 $g/cm^3$ to about 0.40 $g/cm^3$ the storage core 32 is preferably mechanically flexed or otherwise manipulated to make it more flexible before it is placed in use. The above densities are the "in bag" densities of the storage core in packaged diapers measured under a pressure of about 1.8 psi (about 132 $g/cm^2$).

(For simplicity, the density values specified above do not include the weight of any particles of absorbent gelling material. The density of the storage core has been specified in this manner because the amount of absorbent gelling material can vary within a fairly wide range in the various different embodiments. The overall density of the storage core, thus, will be greatly affected by the amount of absorbent gelling material in the storage core, making it impractical to attempt to express an all-inclusive overall range of density for the storage core.)

(e) Examples of Alternative Storage Cores

In one preferred sanitary napkin embodiment, the storage core 32 is an air-laid blend comprised of approximately 15% of 0.5 inch long, 15 denier per filament crimped polyester fibers and approximately 85% of cross-linked cellulose fibers. The polyester fibers are preferably crimped at a crimping frequency of about 6 crimps per linear inch and at a crimping angle of about 90°. The storage core 32 is preferably compressed to a density of about 1 g/cubic inch (about 0.06 $g/cm^3$).

The densification may be applied to the entire storage core 32, or in alternative embodiments, only to selected portions of the storage core. The same applies to the acquisition layer. Patterned densification allows tailoring of the liquid handling properties to a specific need. For example, the density may be very low in the liquid target area to maximize liquid acquisition speed, and density may be very high near the core edges to maximize liquid wicking.

The storage core 32 may optionally be sprayed with latex to give the storage core added integrity. Latex may be applied by spraying it on one or both faces of the storage core. One latex suitable for this purpose is known as TR 520 available from Rhom & Haas of Philadelphia, Pa. The latex may be heated until it crosslinks or cures.

The storage core 32 may also be treated with a surfactant to increase the ability of the storage core to receive liquids and to transport liquids into and through the storage core. This is useful particularly when the storage core contains a high concentration of synthetic (e.g. polyester) fibers. Suitable surfactants include those known commercially as Brij 76, PEGOSPERSE 200ML, and PLURONIC L92. The surfactant can be applied in any suitable manner. Preferably, the surfactant is applied by spraying it on the body-facing side 32A of the storage core.

(4) Construction of the Multiple Layer Absorbent Structure

The three components of the preferred multiple layer absorbent structure 28, the acquisition layer 30, liquid stable layer 34, and storage core 32, are preferably held together by adhesives applied between the adjacent faces of the components.

The bonds between the components of the multiple layer absorbent structure 28 are shown in detail in FIG. 3. The body-facing side 30A of the acquisition layer 30 is adhered to the underside (or garment-facing side) 24B of the topsheet 24 by adhesive 66. The garment-facing side 30B of the acquisition layer 30 is bonded to the body-facing side 34A of the liquid stable layer 34 by adhesive 67. The garment-facing side 34B of the liquid stable layer 34 is, in turn, bonded to the body-facing side 32A of the storage core 32 by adhesive 68. The multiple layer absorbent structure 28 is also preferably adhered between the topsheet 24 and backsheet 26 by adhesives shown as layers 66 and 69. These adhesives are applied between the multiple layer absorbent structure 28 and the respective inwardly-facing surface (or garment-facing side) 24B of the topsheet 24 (as described above) and the body-facing side 26A of the backsheet 26.

The adhesives are shown schematically as layers in FIG. 3 for simplicity. The adhesives, however, need not be applied only in the form of layers. The adhesives can be applied in any of the manners described with relation to the adhesives used to bond the acquisition layer to the topsheet (e.g., spirals, etc.). In addition, other types of attachment means can be used. The components of the multiple layer absorbent structure can be adhered together by any of the attachment means that are described above with relation to adhering the acquisition layer to the topsheet. It should also be understood that the various different layers of the multiple layer absorbent structure need not all be attached by the same type of attachment means. The layers of the multiple layer absorbent structure can be attached to each other by different attachment means and/or if adhesives are used, different types of adhesive applications/patterns can be used between layers. In the preferred embodiment shown in FIG. 3, the layers of the multiple layer absorbent structure are preferably held together by an open pattern network of adhesive filaments comprising several lines of adhesive filaments swirled into a spiral pattern.

The crimped synthetic fibers 48 serve an important role in the wet integrity of the components of the multi-layer absorbent structure 28. The crimped synthetic fibers 48 in the acquisition layer 30 and storage core 32 should preferably be long enough to form at least portions of the surfaces of these respective components. The synthetic fibers will typically be long enough to form at least a portion of the surface of a given layer if they have lengths that range from lengths which are equal to the thickness of the layer that they comprise up to lengths that are greater than or equal to 50% more than the thickness of the layer they comprise.

The synthetic fibers (or portions thereof) that form part of the surface of the acquisition layer and the storage core are available to be bonded with adhesives to the adjacent layers. Since the synthetic fibers are moisture insensitive, they will be able to form liquid stable bonds (shown as elements 70) to the topsheet 24. This will ensure that the bonds do not fail when the diaper is wetted by bodily exudates. Liquid stable bonds 70 will also be formed between the garment-facing surface 30B of the acquisition layer 30 and the liquid stable layer 34 (or if there is no intermediate liquid stable layer, to the body-facing surface 32B of the storage core 32). The crimped synthetic fibers will also form liquid stable bonds 70 between the garment-facing surface 34B of the liquid stable layer 34 and the body-facing surface 32A of the storage core 32. Liquid stable bonds 70 will also be formed between the garment-facing surface 32B of the storage core 32 and the body-facing surface 26A of the backsheet 26.

The topsheet, liquid stable layer, and backsheet are also liquid stable in that they generally resist stretching when wet and are able to serve as supporting substrates for the other layers such as the acquisition layer 30 and the storage core 32. The acquisition layer 30 and the storage core 32 are nonwoven, and are thus, subject to stretching and being pulled apart under the forces associated with wearing of the diaper and loading of the diaper with bodily liquids. The acquisition layer 30 and storage core 32 of the present invention, however, are bonded to these liquid stable layers at fixed liquid stable bond sites 70. The acquisition layer and storage core are, thus, in effect, anchored to the topsheet, backsheet, and intermediate liquid stable layer in such a manner that the bonding ties these nonwoven layers to liquid stable layers. The acquisition layer and storage core are, as a result, able to utilize the resistance to stretching of the adjacent substrates to resist intra-layer separation (e.g., failing by an elongation or strain-related failure mechanism) due to the forces associated with wearing of the diaper such as bending of the diaper, baby activity, and loading of the diaper with liquids.

The construction of the multiple layer absorbent structure described above, thus, provides an interlocking, compression resistant, liquid stable matrix of synthetic fibers and liquid stable components that are inter-connected and remain inter-connected during use. The multiple layer absorbent structure 28 is, thus, resistant to both compression and to tensional forces (i.e., strain-related forces) so that it maintains its void volume and can stay in its prior-to-use condition when wetted and under the loads associated with wearing the absorbent article.

(5) Examples of Alternative Multiple Layer Absorbent Structure

In alternative embodiments, the diaper (or other absorbent article) 20 could also include any additional layers or other components such as are described in the patents incorporated by reference. In a layered construction, one or more layers can consist of all cellulose or cellulose/hydrogel-forming polymer material blends. The layers could also have differing fiber and/or absorbent gelling material content. For example, a higher percentage of absorbent gelling material could be provided in the lower layers to provide additional liquid storage capacity.

In addition, other suitable absorbent core arrangements are described in U.S. Pat. Nos. 4,988,344 and 4,988,345, and European Patent Application Publication No. 0 198 683, published Oct. 22, 1986 in the name of Duenk, et al. Other possible core materials are described in U.S. Pat. No. 4,475,911 issued to Gellert on Oct. 9, 1984. The configuration and construction of the storage core and multiple layer absorbent structure may also be varied (e.g., the storage core and multiple layer absorbent structure may have varying caliper zones, a hydrophilic gradient, a superabsorbent gradient, or lower average density and lower average basis weight acquisition zones; or may comprise one or more layers or structures). The total absorbent capacity of the storage core and multiple layer absorbent structure 28 should, however, be compatible with the design loading and the intended use of the diaper 20. Further, the size and absorbent capacity of the storage core and multiple layer absorbent structure 28 may be varied to accommodate wearers ranging from infants through adults. The multiple layer absorbent structure 28 may have other features such as are described in U.S. Pat. 4,610,678 entitled "High-Density Absorbent Structures" issued to Weisman et al. on Sept. 9, 1986; U.S. Pat. No. 4,673,402 entitled "Absorbent Articles With Dual-Layered Cores" issued to Weisman et at. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

(6) Mechanisms by Which the Storage Core and the Multiple-Layer Absorbent Structure are Believed to Enhance Performance of the Diaper The blended storage core 32 is believed to provide the diaper 20 with enhanced performance. The blended storage core is believed to provide improved liquid acquisition speed and absorptive capacity. These improvements are believed to result in reduced leakage. The storage core can also be made smaller and thinner to make the diaper more comfortable and discrete to wear. The strength of the storage core is also believed to be improved because of the longer crimped synthetic fiber content. Without wishing to be bound to any particular theory, these improved characteristics are believed to be due to a number of factors.

The blended storage core has a lower wet density than cores composed entirely of cellulose. The lower wet density results from the presence of the synthetic fibers. Water is not absorbed into the synthetic fibers, therefore, the modulus of the synthetic fibers does not change when wetted and they do not collapse. The lower wet density provides the blended storage core with improved liquid acquisition speed and higher absorptive capacity. The lower wet density also allows any hydrogel-forming polymer materials included in the fiber matrix to absorb a higher quantity of liquids since there is more room for the polymer materials to swell.

The first group of fibers in the blended storage core 32 is believed to aid in reducing leakage. The blended storage core provides a quantity of small capillaries that a comparable storage core which is comprised of 100% of larger denier synthetic fibers (the type of fibers described as being suitable for use as the second group of fibers) would not have. These smaller capillaries allow the core to pull liquids through the topsheet and away from the wearer's skin. This improves leakage performance due to a reduction in the volume of fluid which can exit the product by running along the surface of the topsheet and the surface of the wearer's skin.

The first group of fibers of the blended storage core also provides a wicking capability. This capability results from the small capillaries mentioned above. This capillarity can be enhanced by densification of the core. The cellulose allows the core to be maintained at a high density when dry that is generally not achievable with pure synthetics. The presence of the synthetic fibers allows the portions of the core that are wetted to expand. This reduces the density of these wetted portions. The neighboring densified areas which are still dry have a high density. This provides these neighboring dry areas with small capillaries. The liquids will, as a result, tend to wick into these neighboring areas. This maintains absorptive capacity and acquisition speed, and also dries the surface of the diaper.

The crimped synthetic fibers are also believed to provide the storage core with improved compression resistance and resiliency. The resiliency maintains the void space in the storage core even after liquids are absorbed into the storage core and pressure is applied to the storage core. The void space provides additional storage space for absorbed liquids. It also provides additional space in which the absorbent gelling materials can swell after taking in liquids.

The multiple layer absorbent structure 28 shown in FIGS. 1–3 is characterized in that it can be made thinner, softer, and more flexible in comparison to absorbent structures made of the same components but that do not contain any crimped synthetic fibers. This can be done while retaining the same performance level as such absorbent structures. The thinness allows the diaper to fit the wearer's body more closely. It also allows groups of diapers to be fit into smaller, more convenient packages.

For example, in the preferred embodiment shown in FIG. 3, the acquisition layer 30 preferably has an "in bag" caliper of between about 0.035 inches (about 0.089 cm) and about 0.060 inches (about 0.15 cm), or less. In this embodiment, the liquid stable layer 34 preferably has an in bag caliper of between about 0.001 inches (about 0.0025 cm) and about 0.004 inches (about 0.01 cm), or less. The storage core 32 preferably has an in bag caliper of between about 0.050 inches (about 0.13 cm) and about 0.085 inches (about 0.22 cm), or less. The in bag caliper is measured under a pressure of about 1.8 psi. It should be understood that the in bag pressure can be thought of as a confining pressure that will prevent the diapers from expanding beyond the above dimensions. It should be understood that it generally requires a larger pressure to initially place the diapers into the bag.

The total in bag caliper of the multiple layer absorbent structure 28 is, thus, between about 0.086 inches (about 0.22 cm) and about 0.15 inches (about 0.38 cm), or less. (These dimensions can be compared with the relevant dimensions of previous diapers sold by The Procter & Gamble Company under the trademarks PAMPERS PHASES and LUVS PHASES. Such diapers have absorbent structures with total in bag calipers which range from about 0.151 inches (about 0.381 cm) and about 0.236 inches (about 0.6 cm). It should, however, be understood that the present invention is not limited to diapers with such dimensions.

The multiple layer absorbent structure 28 can also provide the diaper with improved integrity, resiliency, and liquid processing capability in comparison to absorbent structures that do not contain any crimped synthetic fibers. The improved integrity allows the multiple layer absorbent structure 28 to resist bunching, roping, cracking and layer separation during use. The improved resiliency allows the multiple layer absorbent structure 28 to resist compression during use so that the fibers which form the absorbent matrix (or absorbent system) to maintain space therebetween (i.e., the absorbent matrix remains open) to promote better liquid processing. The increased liquid processing capability is believed to permit the use of less fiber and superabsorbent material. The use of less fiber and superabsorbent material can result in a cost savings.

The improvements to the integrity, resiliency, and liquid processing capability provided by the multiple layer absorbent structure are described in greater detail below with reference to FIGS. 4–7.

Figure 4:
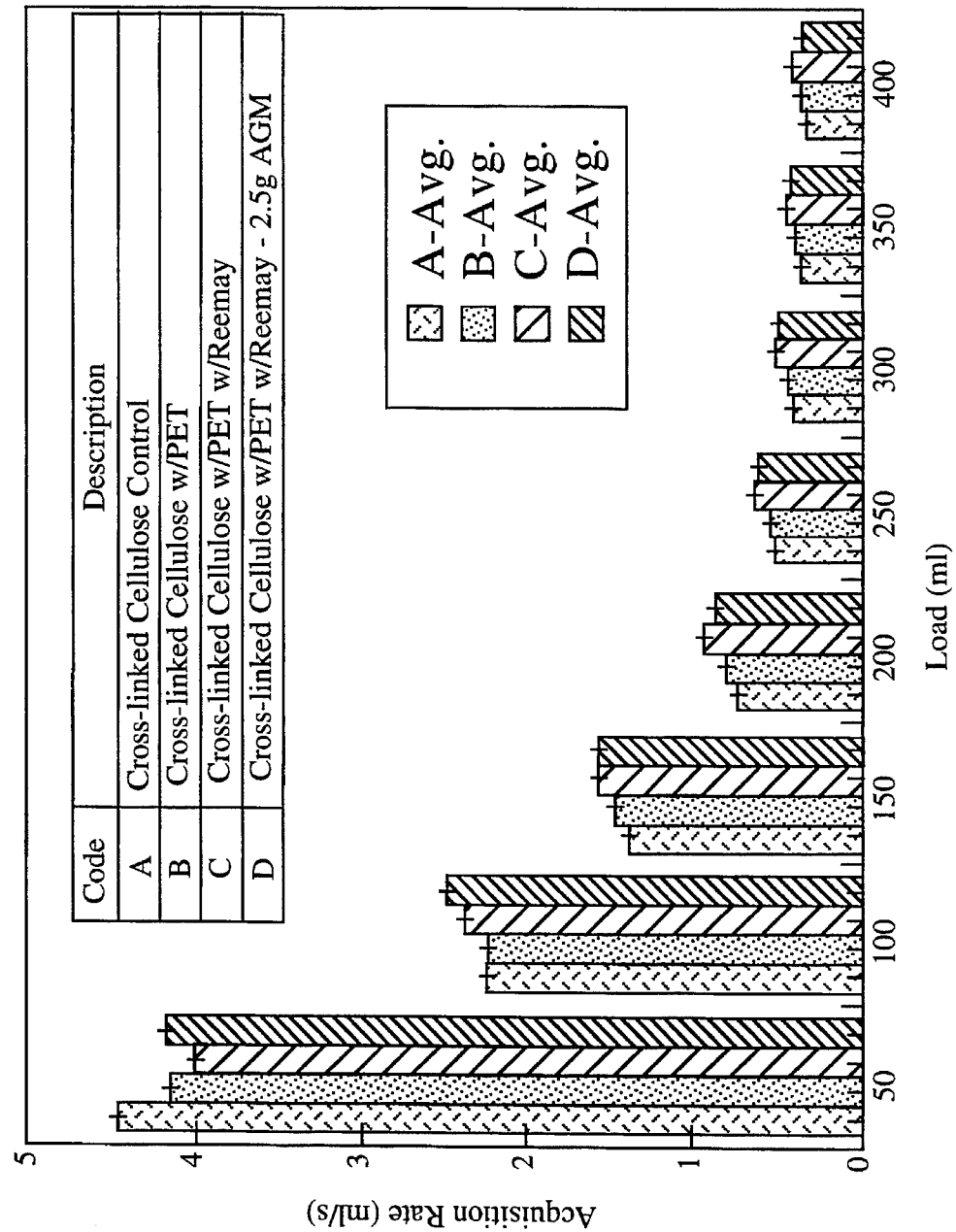
FIG. 4 is a graph which shows the acquisition rate of diapers having several different types of multiple layer absorbent structures versus liquid loading.

FIG. 4 is a bar graph which shows the acquisition rates of several diaper embodiments. The acquisition rates of the diapers shown in FIG. 4 are measured by the Acquisition Test set out in the "Test Methods" section of this specification (Section 4 below). The acquisition rate is provided for four different diaper embodiments. The four diapers shown in FIG. 4 are: (1) a diaper comprising an acquisition patch of cross-linked cellulose fibers, an intermediate layer comprising a conventional tissue, and a storage core comprising a blend of airfelt and absorbent gelling material (the control product); (2) a diaper similar to the control diaper but which is provided with an acquisition patch comprising an 80%/20% blend of cross-linked cellulose fibers and PET fibers instead of airfelt; (3) a diaper similar to diaper number (2) in which the conventional tissue layer is replaced with a REEMAY web; and, (4) a diaper similar to diaper number (3) in which 2.5 grams of absorbent gelling material have been removed from the diaper. FIG. 4 shows that after 100 ml of synthetic urine is loaded on the diaper, diapers numbered (2) though (4) perform at least as well as the control diaper. FIG. 4 further shows that the acquisition rate of the diaper with the 2.5 grams of absorbent gelling material removed from the same is not significantly adversely affected by the reduction in absorbent gelling material.

Figure 5:
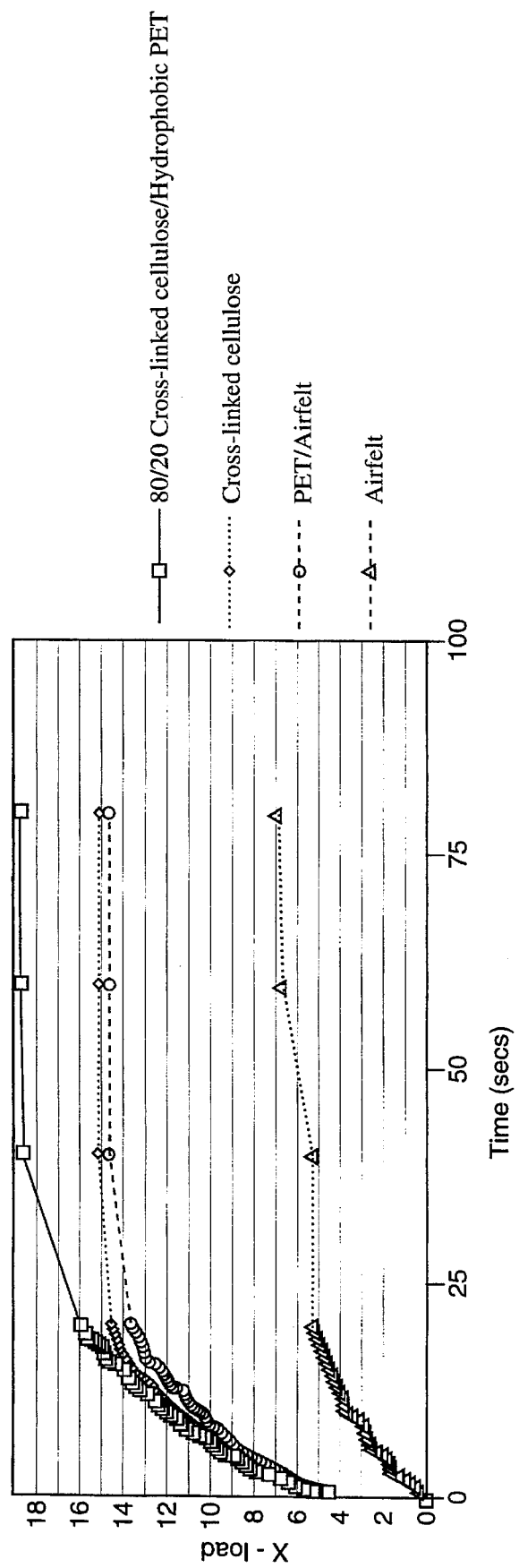
FIG. 5 is a graph which shows the X-Y plane demand acquisition rate of several different absorbent materials.

FIG. 5 is a graph which shows the X-Y plane demand acquisition rate of several different absorbent materials. The X-Y plane demand acquisition rate is measured by the Demand Wettability Test (or "Demand Absorbency Test") set out in the "Test Methods" section. The X-Y plane demand acquisition rate is provided for four different 4 inch by 4 inch (10.2 cm by 10.2 cm) samples of acquisition patch materials. The four materials shown in FIG. 5 are: 100% airfelt; an 80%/20% blend of airfelt and crimped PET fibers; 100% cross-liked cellulosic material; and, an 80%/20% blend of cross-linked cellulosic material and crimped PET fibers. The airfelt has a basis weight of 0.19 g/inch$^2$ (0.03 g/cm$^2$) and the other three materials have basis weights between 0.11 to 0.12 g/inch$^2$ (between about 0.017 and about 0.019 g/cm$^2$).

The samples are formed and then the samples are subjected to a 400 psi load for less than one second to simulate calendering the liquid acquisition patch might be subjected to during manufacture. The samples are placed under 0.2 psi during the test to simulate the pressure exerted on a diaper by a baby's body. The results are plotted in the form of X-load (grams of synthetic urine per gram of absorbent gelling material) versus time. A series of curves is depicted in FIG. 5. The slope of the curve is the acquisition rate of the sample. As shown in FIG. 5, the curves level off at a loading at which the samples are saturated.

FIG. 5 shows that the inclusion of 20% hydrophobic crimped PET fibers in an airfelt acquisition layer increases the liquid acquisition rate of the acquisition layer by about 300%. FIG. 5 also shows that the inclusion of 20% hydrophobic crimped PET fibers in a cross-linked cellulose acquisition layer increases the liquid acquisition rate and capacity of the acquisition layer by about 20%. This improvement can, for example, be exploited by providing a diaper with a 20% increase in these properties, or by providing a diaper having a 20% reduction in the basis weight of the acquisition layer.

Figure 6:
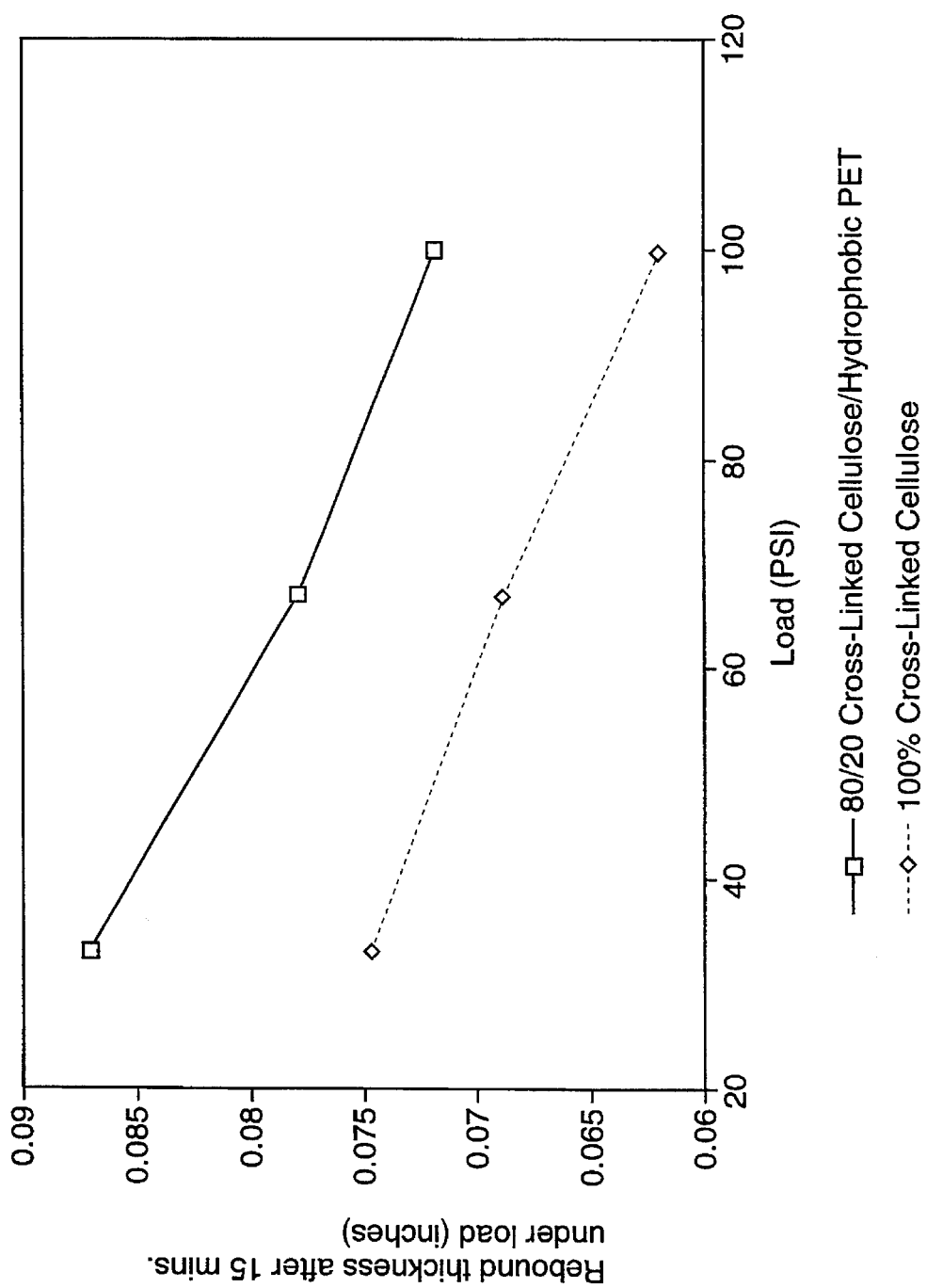
FIG. 6 is a graph which shows the resiliency of two different types of absorbent materials.

FIG. 6 shows the resiliency of two sample patches of acquisition layer material under dry conditions. The resiliency of the sample patches is measured by first subjecting the sample patches to the 400 psi load described above and measuring the caliper of the sample patches. Three identical sample patches are used. One of the samples is then subjected to a pressure of 33 psi for 15 minutes. Another sample patch is subjected to a pressure of 67 psi for 15 minutes. The last sample is subjected to a pressure of 100 psi. for 15 minutes. The pressure is then removed, and the caliper is measured 15 minutes after the pressure has been removed. This procedure is intended to simulate the forces that a diaper may undergo when it is compressed to place the same into a bag during manufacture. The three different pressures are intended to simulate different amounts of compression that may be used in a diaper bagging operation. It is understood, however, that this is only intended to provide an approximation of the effect of a bagging operation on a diaper since in actual conditions a diaper will remain in a bag for much longer periods. The resiliency of the samples under the three different pressures are plotted on FIG. 6. FIG. 6 shows that the inclusion of 20% hydrophobic PET fibers in a cross-linked cellulose acquisition layer improves the resiliency of such a layer by about 15%. This allows the basis weight of the acquisition layer to be reduced if desired, and the increase in resiliency will at least partially offset the effect of the reduction in basis weight.

Figure 6A:
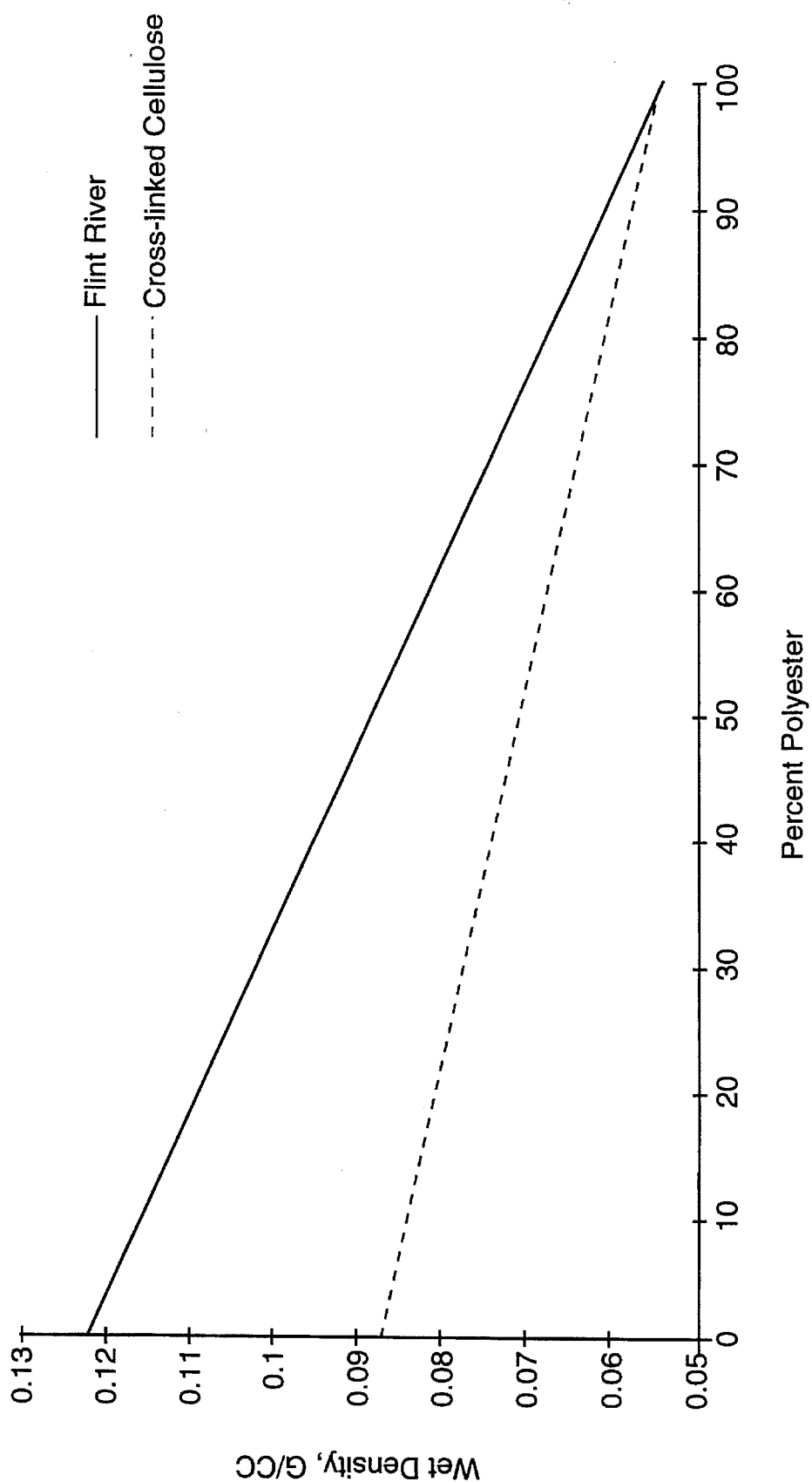
FIG. 6A is a graph which shows the effect of adding different amounts of polyester on the wet density of a web.

FIG. 6A shows the effect of the addition of various percentages of polyester fibers on the wet density of the acquisition layer. FIG. 6A depicts this effect on two different types of acquisition layer material, Flint River fluff and cross-linked cellulose. The acquisition layer material is saturated with synthetic urine. The wet density is measured under a pressure of 96 grams/inch$^2$ (15 grams/cm$^2$). FIG. 6A shows that, in general, the wet density of Flint River fluff is higher than that of the cross-linked cellulose. FIG. 6A also shows that the wet density of both materials decreases in a linear fashion when the acquisition layer contains higher percentages of polyester fibers.

Figure 7:
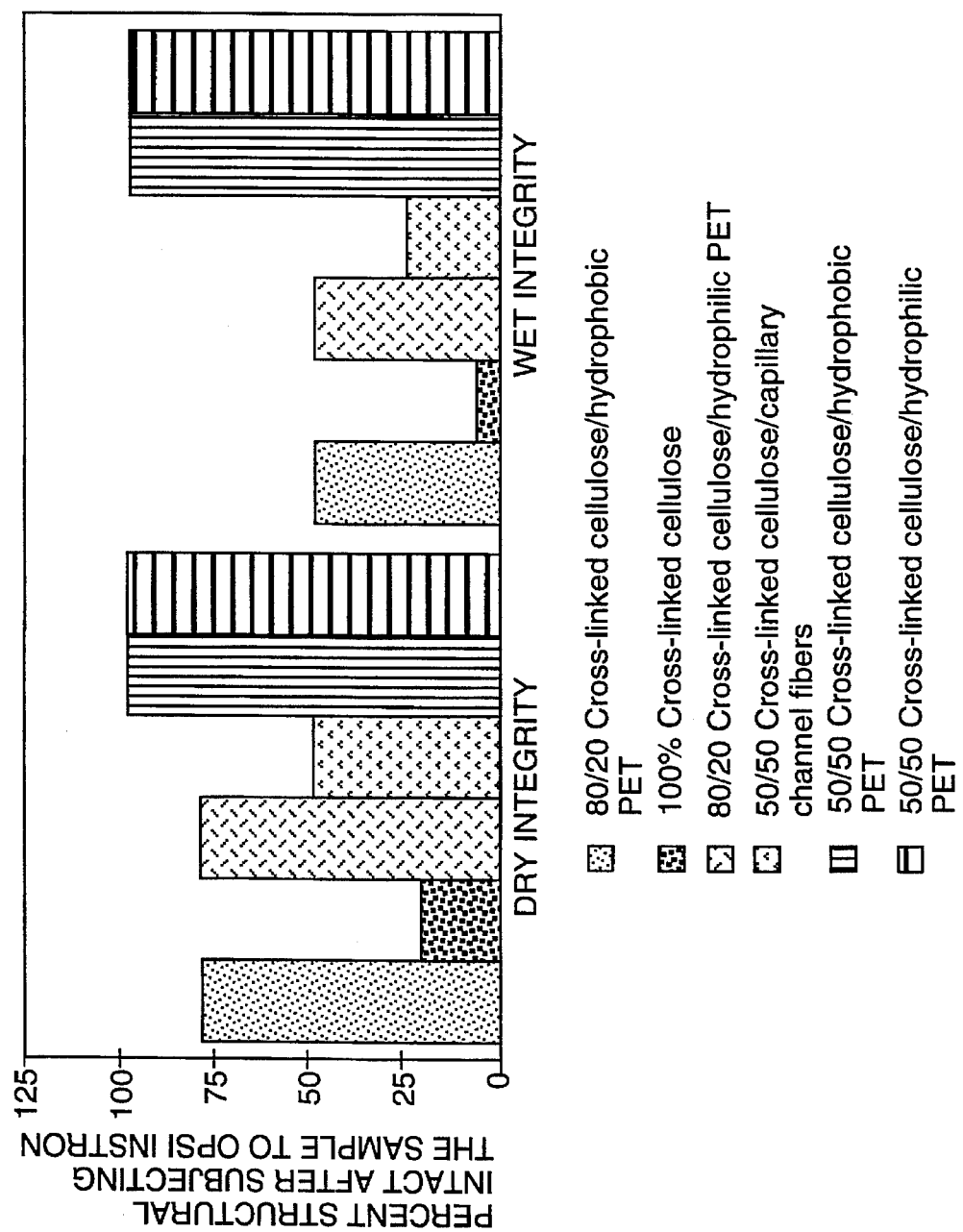
FIG. 7 is a graph which shows the dry and wet structural integrity of several different absorbent materials.

FIG. 7 shows the dry and wet structural integrity of several samples of acquisition layer materials. The structural integrity of the sample patches is measured on 10"×4" rectangular acquisition patches having basis weights of 0.10 –0.12 g/in$^2$. The sample patches are calendared under a pressure of 400 psi for less than one second using a hydraulic press. The samples are then suspended from their shorter end using at least 4 inch (10 cm) wide clamps under free load (that is, only under its own weight) for a 3 minute time period. The dimension of the sample, or fraction of the sample left hanging after the time period is measured in a direction perpendicular to the ground. This measurement is recorded as a rough approximation of the integrity of the sample. The measurement of the sample after this test is expressed as a percentage of the initial 10" length of the sample to provide the percentage dry integrity of the sample. Wet integrity is determined by following basically the same procedure. In the wet integrity test, however, 100 ml of water is poured on the sample before it is suspended. FIG. 7 shows that the inclusion of 20% crimped fibers in a cross-linked cellulose acquisition layer is believed to increase the dry and wet structural integrity of the acquisition layer by about 350% and about 800%, respectively.

The inclusion of crimped PET fibers in the acquisition layer 30 and in the storage core 32, and the provision of the spunbonded polyester nonwoven web between the acquisition layer 30 and the storage core 32, while not wishing to be bound by any particular theory, are believed to improve the integrity of the multiple layer absorbent structure 28 by four mechanisms.

The first mechanism is due to the fact that the crimped PET fibers interlock with each other. The gives tenacity and strength to thin structures through cohesive entanglement of the polyester fibers and the cellulose fibers. This allows for a reduction in basis weight and bulk without losing structural integrity. This method of increasing structural integrity is a departure from conventional theory wherein structural integrity is supplied through high basis weight and bulk. This interlocking enables the entire composite absorbent structure to form a connective matrix of crimped PET fibers that is not as readily subject to collapse as an absorbent structure comprised of 100% airfelt.

The second mechanism results from the fact that the PET fibers are nonabsorbent. The PET fibers will, therefore, retain their strength when the composite absorbent structure becomes wet since the PET fibers are not absorbent. This can be contrasted with cellulose fibers which will tend to lose their strength after absorbing liquids.

The third mechanism deals with the adhesive bonding between the layers of the multiple layer absorbent structure. Adhesives generally bond very well to both dry cellulose fibers and synthetic materials. However, when absorbent layers comprised of cellulosic or cellulosic-based materials become wet, the adhesive bonds to the cellulose-based materials become weak and easily fail. Adhesive bonds to synthetic materials, on the other hand, will generally remain intact when such materials become wet. The reason for the different behavior is that liquids will penetrate the cellulose-based materials and contaminate the adhesive bond interface. This will not happen with the synthetic materials since they do not absorb liquids. Thus, the multiple layer absorbent structure of the present invention is characterized in that the adhesive bonding between the faces of the components remains intact when the multiple layer absorbent structure is wetted.

The fourth mechanism relates to the strength of the substrates to which the individual components are bonded. The individual higher integrity components are now also bonded to high wet tensile strength substrates. The high wet tensile strength of the substrates (e.g., topsheet, backsheet, and intermediate liquid stable layer) limits the elongation of the acquisition layer and the storage core. This allows the substrates to hold the fiber spacing more constant within the acquisition layer and storage core and to transfer most of the loading forces exerted on the nonwoven components of the multiple layer absorbent structure to the high wet tensile strength substrates.

The adhesive bonding and fiber interlocking is believed to allow the diaper to remain closer to its intended configuration during use. The layers of the diaper will be less likely to separate during use due to the failure of the adhesive bonds between layers. The multiple layer absorbent structure will also be less likely to shift around since it will be held firmly in place within the diaper chassis (i.e., between the topsheet and backsheet). The bonds of the multiple layer absorbent structure to the diaper chassis will also tend to inhibit the bunching and roping of the multiple layer absorbent structure. In addition, the adhesive bonds between the layers and the interlocking fibers within the layers will also tend to resist cracking and fracturing of the multiple layer absorbent structure.

The inclusion of the synthetic fibers (which are typically white in color) can, in addition to the above benefits, also be used to make the individual layers have a higher degree of whiteness, and to thus have the appearance of being cleaner.

D. The Backsheet

The backsheet 26 prevents the exudates absorbed and contained in the multiple layer absorbent structure 28 from wetting articles which contact the diaper 20 such as clothing, bedsheets, and undergarments. The backsheet 26 is impervious to liquids (e.g., urine). The backsheet 26 may comprise a woven or nonwoven material, polymeric films such as thermoplastic films of polyethylene or polypropylene, or composite materials such as a film-coated nonwoven material. The backsheet 26 is preferably manufactured from a thin plastic film, although other flexible liquid impervious materials may also be used. As used herein, the term "flexible" refers to materials which are compliant and will readily conform to the general shape and contours of the human body.

Preferably, the backsheet is a thermoplastic film having a thickness of from about 0.012 mm (0.5 rail) to about 0.051 mm (2.0 mils). Particularly preferred materials for the backsheet include RR8220 blown films and RR5475 cast films as manufactured by Tredegar Industries, Inc. of Terre Haute, In. The backsheet 26 is preferably embossed and/or matte finished to provide a more clothlike appearance. Further, the backsheet 26 may permit vapors to escape from the multiple layer absorbent structure 28 (i.e., breathable) while still preventing exudates from passing through the backsheet 26.

The backsheet 26 is positioned adjacent the surface of the multiple layer absorbent structure 28 that faces away from the wearer's body and is preferably joined thereto by attachment means known in the art and described above in conjunction with the description of the manner in which the acquisition layer is attached to the topsheet. The attachment means preferably comprises an open pattern network of filaments of adhesive as is disclosed in U.S. Pat. No. 4,573,986 entitled "Disposable Waste-Containment Garment", which issued to Minetola, et at. on Mar. 4, 1986, and more preferably comprises several lines of adhesive filaments swirled into a spiral pattern.

The diaper 20 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The tape tabs of the fastening system are then released from the release portion. The fastening system is then secured to the outer surface of the diaper to effect a side closure.

3. Alternative Types of Absorbent Articles.

The multiple layer absorbent structure can also be used in other types of absorbent articles, such as training pants, sanitary napkins, panty liners, and adult incontinence devices.

The term "training pant", as used herein, refers to disposable garments having fixed sides and leg openings. Training pants are placed in position on the wearer by inserting the wearer's legs into the leg openings and sliding the training pant into position about the wearer's lower torso. Suitable training pants are disclosed in U.S. Pat. No. 5,246,433 issued to Hasse, et al. on Sept. 21, 1993.

The term "sanitary napkin", as used herein, refers to an article which is worn by females adjacent to the pudendal region that is intended to absorb and contain the various exudates which are discharged from the body (e.g., blood, menses, and urine). Suitable sanitary napkins that can be provided with the multiple layer absorbent structure of the present invention are disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264 and 5,009,653 issued to Osborn on Aug. 21, 1990 and Apr. 23, 1991, respectively; in PCT International Publication No. WO 92/07535 published in the name of Visscher, et al. on May 14, 1992; and in PCT Patent Publication No. WO 93/01785 published Feb. 4, 1993 in the name of Osborn, et al.; and in application Ser. No. 07/966,240 entitled "Absorbent Article Having Blended Absorbent Core" (P&G Case 4750) filed in the name of Ahr, et al. on Oct. 26, 1992 (which also describes other types of absorbent articles as well).

The terms "pantiliner" or "panty liner" refer to absorbent articles that are less bulky than sanitary napkins which are generally worn by women between their menstrual periods. Suitable absorbent articles in the form of pantiliners that can be provided with the multiple layer absorbent structure described herein are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinence articles that can be provided with the multiple layer absorbent structure described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. 4,909,802 issued to Ahr, et al.; U.S. Pat. No. 4,964,860 issued to Gipson, et al. on Oct. 23, 1990; and in application Ser. No. 07/637,090 filed by Noel, et al. on Jan. 3, 1991 (PCT Publication No. WO 92/11830 published on Jul. 23, 1992).

4. Test Methods

A. Acquisition Test

The rate at which an absorbent article such as a diaper is able to acquire liquids is measured by the following Acquisition Test which has been developed for this particular purpose.

PRINCIPLE

This test simulates the introduction of urine into a diaper under the following conditions:

1) A pressure of 0.4 psi (about 28 $g/cm^2$) is applied to a diaper sample.

2) A total of 4 or more 50 cc loadings of synthetic urine at a rate of 10 ml/second are applied to the diaper sample, with a 5 minute time period (equilibration time) between each loading.

| APPARATUS | |
|---|---|
| Conditioned room | Temperature and humidity controlled with the following limits: Temperature: 73 ± 2° F. Relative Humidity: 50 ± 2% |
| Acquisition Tester | Obtain from Concord - Renn Co., 6315 Warrick St., Cincinnati, OH. 45227. Part Test Bed (PLEXIGLAS) Foam Base - 6" × 20" × 1" foam covered with polyethylene backsheet material - foam type: Density 1.0 $lb/ft^3$. IDL 24 psi Nozzle Cover plate 10# weights (need 4) 6.5# weights (need 2) 5# weights (need 2) 2# weights (need 2) |
| Graduated cylinders (100 ml) (1,000 ml) | VWR Scientific, (100 ml) Catalog number: 24711-310 (1,000 ml) Catalog number: 24711-364 or equivalent |
| Erlenmeyer flask (6,000 ml) | VWR Scientific Catalog number: 29135-307 or equivalent |
| Scissors | Convenient source |
| Digital Pump | Cole-Parmer Instrument Co.; Tel. No. (800) 323-4340 Catalog number: G-07523-20 |
| Easy Load Pump Head | Cole-Parmer Instrument Co. Catalog number: g-07518-02 |
| Distilled water | Convenient source |
| Dry Synthetic Urine | Jayco SynUrine |

ASSEMBLY OF TEST APPARATUS

Figure 8:
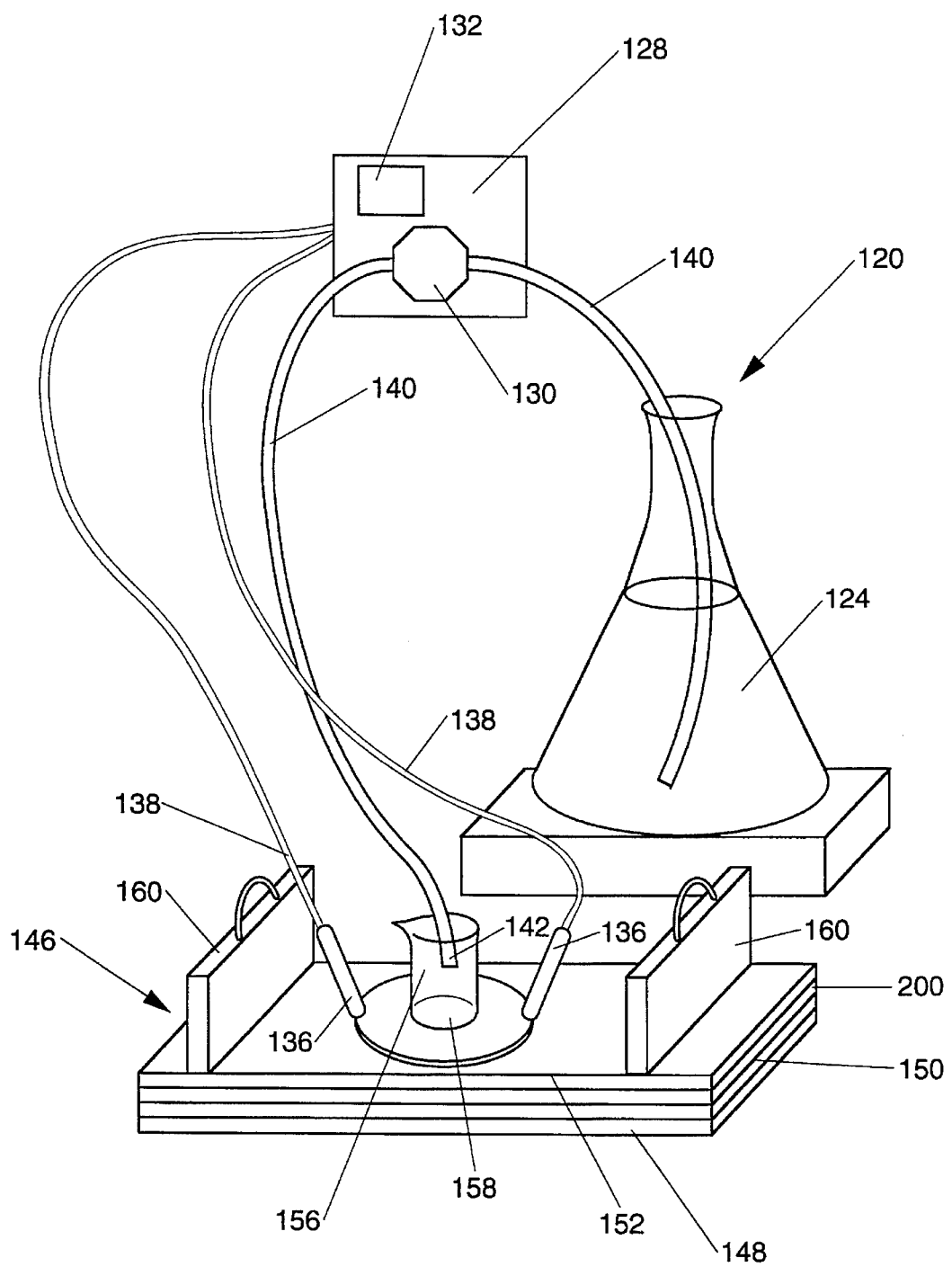
FIG. 8 is a schematic view of the apparatus used in the Acquisition Test.

The test apparatus should be assembled as shown in FIG. 8. The test apparatus, as shown in FIG. 8, is designated by reference number 120. The test apparatus 120 is placed on a suitable table or bench top. The test apparatus 120 comprises a supply of synthetic urine 124, a pump 128, a pair of electrical connectors (or probes) 136, and a sample holder 146.

The pump 128 is a volumetric pump which is equipped with a pump head 130 and digital timer 132. The electrical probes 136 are connected to the pump 128 by wires 138. Rubber tubing 140 runs from the supply of synthetic urine 124 to the pump 128 and from the pump 128 to the sample holder 146. The rubber tubing 140 that runs from the pump 128 to the sample holder 146 may be held over the sample holder 146 by a ring stand (not shown). The end of the rubber tubing 140 that runs to the sample holder 146 also contains a nozzle 142 for directing the synthetic urine onto the sample.

The sample holder 146 comprises a PLEXIGLAS test bed, a foam base 150, and a cover plate 152. The test bed 148 is shown schematically in FIG. 8 as comprising a PLEXIGLAS base plate for simplicity. The test bed 148 should also have four PLEXIGLAS walls which stand upright from the base and surround the diaper sample 200. This prevents synthetic urine from running out of the test bed 148 during the test. The foam base 150 is placed on top of the PLEXI- GLAS base plate 148 so that the pressure on the sample will be equalized during the test. A diaper sample 200 is placed on the foam base with its topsheet facing upward. The cover plate 152 is then placed on top of the diaper sample so that the cylindrical liquid directing column 156 and opening 158 in the cover plate are in the center of the diaper sample. Weights 160 are then placed on the cover plate 152 so that a pressure of 0.4 psi is applied to the diaper sample.

The electrical probes 136 are arranged so that they just touch the topsheet of the diaper sample in the region where synthetic urine is deposited. The electrical probes are located outside, and on opposite sides of the cylindrical liquid directing column 156. The electrical probes 136 detect the presence of synthetic urine on the topsheet of the diaper sample. When all of the synthetic urine has been acquired by the diaper sample, the electrical connection between the electrical probes 136 will be broken. This will provide the time for the diaper sample to acquire a given amount of synthetic urine.

SYNTHETIC URINE PREPARATION

Measure four 1,000 ml portions of distilled water into a clean, dry 6,000 ml Erlenmeyer flask. Add a stirring bar to the flask and place the flask on a magnetic stirring plate. Carefully transfer the dry synthetic urine mixture into the flask containing the 4,000 ml of distilled water. A funnel is very helpful in preventing loss of the dry synurine mixture. Rinse the funnel into the Erlenmyer flask with the last 1,000 ml portion of distilled water so that a total of 5,000 ml of distilled water is added to the flask. Allow the solution to stir until all solids are dissolved.

Label and date the flask; discard any solution remaining after 7 days.

Larger volumes of synthetic urine (multiples of 5,000 ml) may be made if greater volumes are required. Use appropriately larger volumes of distilled water (for example, 10,000 ml in a 12,000 ml container) and the appropriate number of dry synurine mixture packages (e.g., 2 packages for 10,000 ml).

PROCEDURE

1) Cut any elastics out of the diaper so that the diaper will lay flat. Place the diaper on top of the piece of foam in the acquisition tester base. The diaper should be placed with the topsheet of the diaper facing upward, so that the synthetic urine will be applied to the topsheet.

2) Place the cover plate assembly on the diaper.

3) Gently place the appropriate weights on the cover plate so that a pressure of 0.4 psi is placed on the diaper.

4) Move the ring stand into position so that the nozzle is directly above the center of the cylindrical liquid directing column. Lower the ring until the nozzle extends 2" (about 5 cm) above the surface of the diaper. Position the nozzle so that it is perpendicular to the bench top.

5) Start the pump.

6) The pump will begin dispensing the specified volume of synthetic urine, and the timer will run until that volume has been absorbed by the diaper. When all of the fluid has been absorbed by the diaper, the Acquisition Time for the volume of synthetic urine added will appear on the digital pump.

7) After a 5 minute equilibration time has elapsed, the test cycle will automatically repeat. The test cycle will run the desired number of times so that a specific volume of synthetic urine is applied to the diaper sample.

8) After completing all of the tests, run distilled water through the tubing. Clean the surface of the small probe contacts located inside the base of the top plate tube with a small brush on a daily basis. If the acquisition tester is being used around the clock and it is not possible to rinse the synthetic urine out of the tubing, replace the tubing monthly. Replace the foam base every 3 months to maintain firmness of support.

B. Demand Wettability Test

The rate at which the material used in the acquisition layer 34 can acquire and distribute fluids is measured by a test which has been developed for this particular purpose. This test is known as the X-Y Plane Demand Wettability Test (or "Demand Absorbency Test").

This method consists of a version of a standard demand wettability test. For reference, standard demand absorbency tests are described in Chatterice, P. K. (Ed.) Absorbency, Chaper II, pp. 60–62, Elsevier Science Publisher B. V., Amsterdam, The Netherlands (1985).

Figure 10:
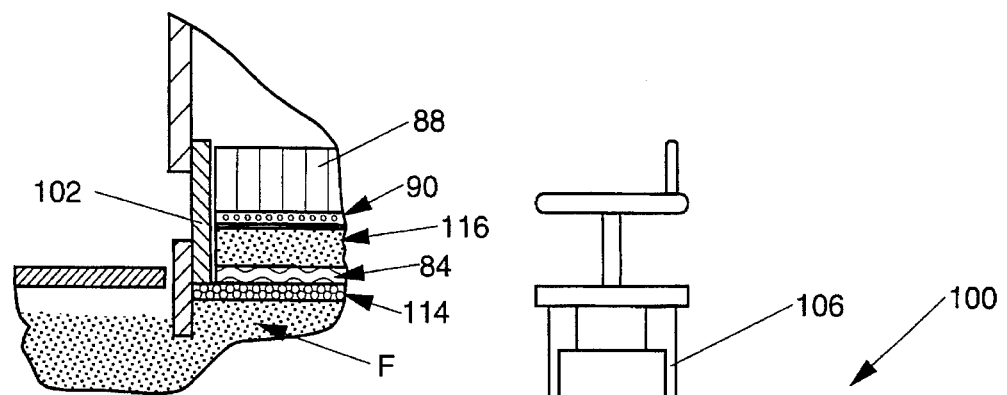
FIGS. 9 and 10 are schematic views of the apparatus used in the Demand Wettability Test.
Figure 9:
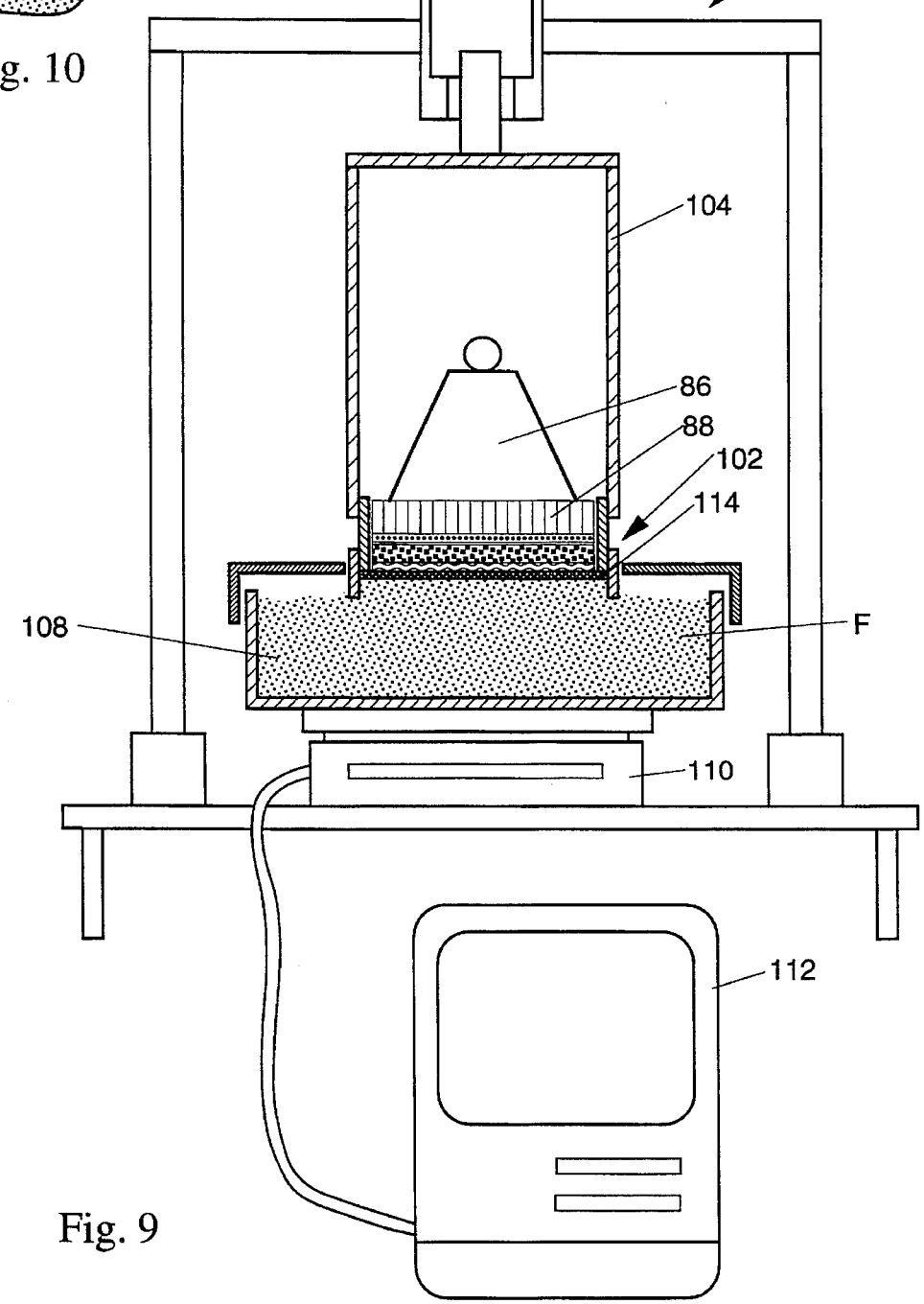

The apparatus used to conduct this test is shown schematically in FIGS. 9 and 10. The apparatus 100 consists of a square sample basket 102 suspended on a frame 104. The inside dimensions of the basket are 4"×4" (10.2 cm.×10.2 cm.). The height of the basket 102 is adjustable via a gear mechanism 106. A fluid reservoir 108 is placed on an electronic balance 110 directly under the sample basket 102. The balance 110 is connected to a computer 112.

Figure 11:
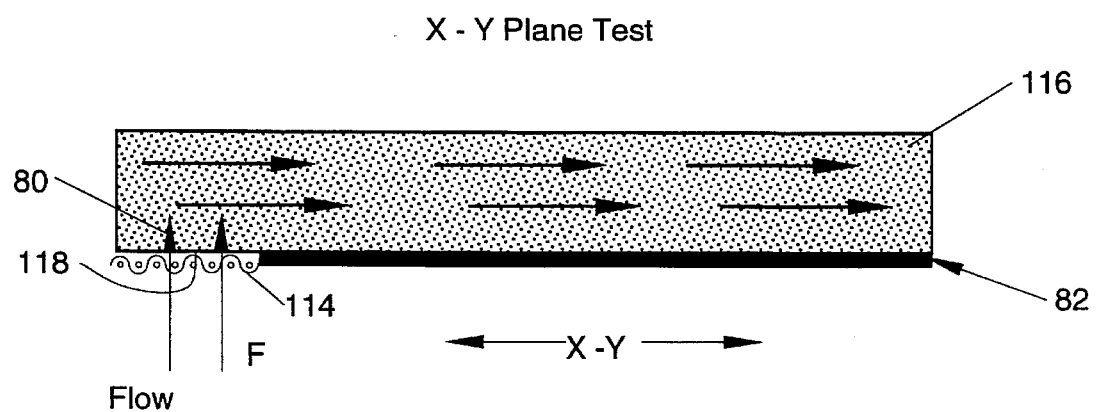
FIG. 11 is an enlarged schematic representation of the flow of liquid in the X-Y plane Demand Wettability Test.

The x-y plane test is shown schematically in FIG. 11. In the x-y plane test, a 1"×4" (2.54 cm.×10.2 cm.) area along one edge 80 of the sample basket bottom consists of a coarse wire screen 114. The portion 118 of the sample 116 overlying the screen contacts the fluid, F, as shown in FIG. 11. (It should be understood that in the context of this description, the term "fluid" means liquid.) The remainder of the sample basket bottom, designated 82, is made of PLEXIGLAS and is liquid impervious. The sides of the sample basket that are in contact with the sample are also made of PLEXIGLAS and are liquid impervious. As shown in FIG. 11, this test requires the sample 116 to first demand the fluid in the z-direction, and then transport it a maximum of 3 inches (7.62 cm.) in the horizontal (x-y) plane. The results from the x-y plane test provide a measurement of the sample's ability to distribute liquid under potential in-use conditions. The x-y plane test is done with the absorbent structure sample 116 confined under a 0.2 psi load applied evenly to the upper surface of the sample 116.

The test procedure is as follows. First, a 4"×4" (10.2 cm.×10.2 cm.) sample of the acquisition layer is cut. The fluid reservoir 108 is filled with about 6800 ml of Synthetic Urine and set on an electronic balance 110 under the test apparatus 100. Then the sample basket 102 is lowered until the fluid level is just at the level near the top of the wire screen 114. A 1"×4" piece of commercially available 2-ply BOUNTY® paper towel 84 is placed on the wire screen 114 in the bottom of the basket 102. The BOUNTY® towel 84 ensures that consistent fluid contact with the underside of the sample 116 is maintained throughout the duration of the test.

The applied weight 86 is attached to a square metal plate 88 with dimensions slightly smaller than the inner dimensions of the sample basket 102. Then the top side of the sample 116 is attached to the bottom of the above-mentioned plate 88 via double sided tape 90, or spray adhesive. At time=zero, the sample 116 is placed into the sample basket 102 and the data acquisition program on the computer is activated. After 100 seconds, the test is stopped and the data analyzed and plotted. This completes the test.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention. It is also expressly not admitted that any of the commercially available materials or products described herein teach or disclose the present invention.

It is to be understood that all of the limits and ranges specified in the foregoing descriptions of the multiple layer absorbent structure include all narrower ranges and limits that are within the specified limits and ranges. Thus, for example, if the denier of a fiber is specified to be between about 2 and about 50, all narrower ranges of denier, such as between about 4 and about 40, and about 10 and about 30, etc., may be claimed even though these ranges are not separately listed. It is, therefore, intended to cover in the appended claims all such changes and modifications that are within the scope of this invention.

While particular embodiments of the present invention have been illustrated and described, it would be obvious to those skilled in the art that various other changes and modifications can be made without departing from the spirit and scope of the invention.

What is claimed is:

1. An absorbent article comprising:

a liquid pervious topsheet;

a liquid impervious backsheet joined to said topsheet;

an absorbent core positioned between said topsheet and said backsheet, said absorbent core comprising a mixture of absorbent gelling material and fibers, said fibers comprising a blend of cellulose fibers and liquid insensitive crimped synthetic fibers comprising about 5% to about 90% by weight of the fibers in said absorbent core, said crimped synthetic fibers having a length of between about 0.6 cm and about 5 cm, a denier of between about 1 ½ and about 40 denier per fiber, and a crimp angle of between about 70° and about 91° as measured between the adjacent portions of a fiber that have a crimp formed therebetween; and an acquisition layer positioned between said topsheet and said absorbent core.

2. The absorbent article of claim 1 wherein said acquisition layer comprises cellulosic fibers.

3. The absorbent article of claim 1 wherein said acquisition layer comprises cross-linked cellulosic fibers.

4. The absorbent article of claim 1 wherein said acquisition layer comprises capillary channel fibers.

5. The absorbent article of claim 1 wherein said crimped synthetic fibers comprise a material selected from the group consisting of: polyester, polypropylene, polyethylene, nylon, viscous rayon, and cellulose acetate.

6. The absorbent article of claim 1 wherein said acquisition layer has crimped synthetic fibers distributed therein.

7. The absorbent article of claims 1 or 6 wherein said crimped synthetic fibers comprise PET fibers.

8. The absorbent article of claims 1 or 6 wherein said acquisition layer is bonded to said topsheet and to said absorbent core by adhesives.

9. The absorbent article of claim 1 further comprising an intermediate layer positioned between said acquisition layer and said absorbent core.

10. The absorbent article of claim 9 wherein said intermediate layer is bonded to said acquisition layer and said absorbent core by adhesives.

11. A multiple layer absorbent structure comprising:

an acquisition layer comprising a blend of a first type of fibers and moisture insensitive crimped synthetic fibers;

an absorbent core beneath said acquisition layer, said absorbent core comprising a mixture of absorbent gelling material and fibers, said fibers comprising a blend of cellulose fibers and liquid insensitive crimped synthetic fibers comprising about 5% to about 90% by weight of the fibers in said absorbent core, said crimped synthetic fibers having a length of between about 0.6 cm and about 5 cm, a denier of between about 1 ½ and about 40 denier per fiber, and a crimp angle of between about 70° and about 91° as measured between the adjacent portions of a fiber that have a crimp formed therebetween, and an additional layer positioned between said acquisition layer and said absorbent core.

12. An absorbent article comprising liquid stable components that retain their integrity when contacted by liquids:

a liquid pervious, liquid stable topsheet;

a liquid impervious, liquid stable backsheet joined to said topsheet;

an absorbent core positioned between said topsheet and said backsheet, said absorbent core having two surfaces which have components of the absorbent article adjacent thereto, said absorbent core comprising at least some liquid insensitive crimped synthetic fibers that can form liquid stable bonds with said adjacent components wherein said liquid stable bonds reta. in their integrity when contacted by liquids; and an acquisition layer positioned between said topsheet and said absorbent core, said acquisition layer having two surfaces which have components of the absorbent article adjacent thereto, said acquisition layer comprising at least some liquid insensitive crimped synthetic fibers that can form liquid stable bonds with said adjacent components, wherein said acquisition layer and said absorbent core are joined at least indirectly to each other through liquid stable bonds and said acquisition layer is joined at least indirectly to said topsheet through liquid stable bonds and said absorbent core is bonded to a liquid stable component.

13. The absorbent article of claim 12 wherein said acquisition layer is bonded directly to said topsheet.

14. The absorbent article of claim 12 wherein said absorbent core is bonded directly to said backsheet.

15. The absorbent article of claim 12 further comprising a liquid pervious intermediate core integrity layer positioned between said acquisition layer and said absorbent core.

16. The absorbent article of claim 15 wherein said acquisition layer is bonded directly to said topsheet and said intermediate layer, and said absorbent core is bonded directly to said intermediate layer and said backsheet.

17. An absorbent article comprising at least the following components:

a liquid pervious topsheet;

a liquid impervious backsheet joined to said topsheet;

an absorbent core positioned between said topsheet and said backsheet, said absorbent core having two surfaces which have components of the absorbent article adjacent thereto and a caliper, said absorbent core comprising a mixture of absorbent gelling material and fibers, said fibers comprising at least some crimped synthetic fibers that can form liquid stable bonds with said adjacent components that retain their integrity when contacted by liquids, said fibers having a length greater than or equal to the caliper of said absorbent core;

an acquisition layer positioned between said topsheet and said absorbent core, said acquisition layer having two surfaces which have components of the absorbent article adjacent thereto and a caliper, said acquisition layer comprising at least some fibers that can form liquid stable bonds with said adjacent components, said fibers having a length greater than or equal to the caliper of the acquisition layer; and a liquid pervious, liquid stable intermediate layer positioned between said acquisition layer and said absorbent core wherein said acquisition layer and said absorbent core are bonded to said intermediate layer.

18. An absorbent article comprising:

a liquid pervious topsheet;

a liquid impervious backsheet joined to said topsheet;

an absorbent core positioned between said topsheet and said backsheet, said absorbent core comprising a mixture of absorbent gelling material and fibers, said fibers comprising a blend of cellulosic fibers and liquid insensitive crimped synthetic fibers comprising between about 5% and about 40% by weight of the fibers in the absorbent core, said crimped synthetic fibers having a denier per fiber of between about 2 and about 30 denier per fiber, an uncrimped length of between about 0.6 cm and about 5 cm, a crimping frequency of between about 5 and about 8 crimps per lineal 2.5 cm, and a crimping angle of between about 60° and about 90° as measured between the adjacent portions of a fiber that have a crimp formed therebetween; and an acquisition layer positioned between said topsheet and said absorbent core, said acquisition layer comprising between about 5% and about 40% by weight of crimped synthetic fibers, wherein at least one of said absorbent core and said acquisition layer is bonded to a liquid stable layer.

19. The absorbent article of claim 18 wherein the crimped synthetic fibers in said acquisition layer have the same characteristics as said crimped synthetic fibers in said absorbent core.

20. The absorbent article of claim 18 wherein the crimped synthetic fibers in said acquisition layer have a higher denier than the crimped synthetic fibers in said absorbent core.

21. The absorbent article of claim 18 wherein said absorbent core and said acquisition layer each have a pair of opposed faces and one of said faces of said acquisition layer is adhesively bonded to one of said faces of said absorbent core.

22. The absorbent article of claim 18 further comprising a spunbonded polyester nonwoven integrity layer positioned between said acquisition layer and said absorbent core.

23. The absorbent article of claim 22 wherein said absorbent core, said nonwoven integrity layer, and said acquisition layer each have two opposed sides, wherein one side of said integrity layer is adhesively bonded to a face of said acquisition layer and the other side of said integrity layer is adhesively bonded to a face of said absorbent core.

24. An absorbent article comprising:

a liquid pervious, liquid stable topsheet;

a liquid impervious, liquid stable backsheet joined to said topsheet;

an absorbent core positioned between said topsheet and said backsheet, said absorbent core having a body-facing face and a garment-facing face, and comprising a homogeneous blend of absorbent gelling material and fibers, said fibers comprising a blend of about 80% by weight of airfelt and about 20% by weight of about 15 denier per fiber, about 1.3 cm long hydrophobic crimped polyethylene terephthalate fibers which are crimped at a frequency of about 6 crimps per lineal 2.5 cm, and at a crimping angle of about 88° as measured between the adjacent portions of a fiber that have a crimp formed therebetween;

an acquisition layer positioned between said topsheet and said absorbent core, said acquisition layer having a body-facing face and a garment-facing face, and comprising a homogeneous blend of about 80% by weight of fibers selected from a group consisting of cellulose fibers and cross-linked cellulosic fibers, and about 20% by weight of said crimped polyethylene terephthalate fibers; and a spunbonded nonwoven polyester liquid stable integrity layer positioned between said acquisition layer and said absorbent core, said integrity layer having two sides, wherein one side of said integrity layer is adhesively bonded to the garment-facing face of said acquisition layer and the other side of said integrity layer is adhesively bonded to the body-facing face of said absorbent core, wherein the body-facing face of said acquisition layer is adhesively bonded to said topsheet and said garment-facing face of said absorbent core is adhesively bonded to said backsheet.

* * * * *